(12) United States Patent
Stadelman et al.

(10) Patent No.: US 8,043,984 B2
(45) Date of Patent: Oct. 25, 2011

(54) SINGLE SIDED STRETCH BONDED LAMINATES, AND METHODS OF MAKING SAME

(75) Inventors: Bryan J. Stadelman, Alpharetta, GA (US); Braulio A. Polanco, Roswell, GA (US); Joerg Hendrix, Alpharetta, GA (US); Peter M. Kobylivker, Marietta, GA (US); Peiguang Zhou, Appleton, WI (US); Bryon P. Day, Canton, GA (US); Wing-Chak Ng, Suwanee, GA (US); Steven R. Stopper, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1472 days.

(21) Appl. No.: 11/011,439

(22) Filed: Dec. 14, 2004

(65) Prior Publication Data
US 2005/0170729 A1 Aug. 4, 2005

Related U.S. Application Data

(63) Continuation-in-part of application No. 10/750,295, filed on Dec. 31, 2003, now Pat. No. 7,601,657.

(51) Int. Cl.
*D04H 3/00* (2006.01)
*D04H 1/00* (2006.01)
*D04H 1/74* (2006.01)
*B32B 5/26* (2006.01)

(52) U.S. Cl. ........ 442/328; 442/329; 442/340; 442/346; 442/366

(58) Field of Classification Search .............. 442/328, 442/329, 366, 400, 381; 428/340
See application file for complete search history.

(56) References Cited

U.S. PATENT DOCUMENTS
2,206,761 A 7/1940 Bergstein
(Continued)

FOREIGN PATENT DOCUMENTS
CA 2165486 6/1996
(Continued)

OTHER PUBLICATIONS

Adhesive Compounds, Encyclopedia of Polymer Science and Technology, Copyright 2002, John Wiley and Sons.*

(Continued)

*Primary Examiner* — Angela Ortiz
*Assistant Examiner* — Jennifer Steele
(74) *Attorney, Agent, or Firm* — Dority & Manning, P.A.

(57) ABSTRACT

An elastic laminate capable of being rolled for storage and unwound from a roll when needed for use, includes an elastic layer of an array of continuous filament strands with meltblown deposited on the continuous filament strands, and a facing layer bonded to only one side of the elastic layer. The meltblown layer may include an elastic polyolefin-based meltblown polymer having a degree of crystallinity between about 3% and about 40%. The laminate suitably has an interlayer peel strength of less than about 70 grams per 3 inches cross-directional width at a strain rate of 300 mm/min. Alternatively or additionally, the continuous filament strands and/or the facing layer may include an elastic polyolefin-based meltblown polymer having a degree of crystallinity between about 3% and about 40%. In certain embodiments, the elastic laminate may include an extensible facing layer bonded to an elastic or semi-elastic film layer having a basis weight of about 50 gsm or less, wherein the facing layer includes an elastic polyolefin-based polymer having a degree of crystallinity between about 3% and about 40%.

29 Claims, 6 Drawing Sheets

U.S. PATENT DOCUMENTS

| | | |
|---|---|---|
| 2,266,761 A | 12/1941 | Jackson, Jr. et al. |
| 2,357,392 A | 9/1944 | Francis, Jr. |
| 2,464,301 A | 3/1949 | Francis, Jr. |
| 2,483,405 A | 10/1949 | Francis, Jr. |
| 2,957,512 A | 10/1960 | Wade et al. |
| 2,957,852 A | 10/1960 | Frankenburg et al. |
| 3,186,893 A | 6/1965 | Mercer |
| 3,338,992 A | 8/1967 | Kinney |
| 3,341,394 A | 9/1967 | Kinney |
| 3,371,668 A | 3/1968 | Johnson |
| 3,391,048 A | 7/1968 | Dyer et al. |
| 3,439,085 A | 4/1969 | Hartmann |
| 3,449,187 A | 6/1969 | Bobkowicz |
| 3,468,748 A | 9/1969 | Bassett |
| 3,489,148 A | 1/1970 | Duncan et al. |
| 3,502,538 A | 3/1970 | Petersen |
| 3,502,763 A | 3/1970 | Hartmann |
| 3,542,615 A | 11/1970 | Dobo et al. |
| 3,575,782 A | 4/1971 | Hansen |
| 3,616,129 A | 10/1971 | Sager |
| 3,629,047 A | 12/1971 | Davison |
| 3,669,823 A | 6/1972 | Wood |
| 3,673,026 A | 6/1972 | Brown |
| 3,676,242 A | 7/1972 | Prentice |
| 3,689,342 A | 9/1972 | Vogt et al. |
| 3,692,618 A | 9/1972 | Dorschner et al. |
| 3,752,613 A | 8/1973 | Vogt et al. |
| 3,773,590 A | 11/1973 | Morgan |
| 3,802,817 A | 4/1974 | Matsuki et al. |
| 3,806,289 A | 4/1974 | Schwarz |
| 3,836,416 A | 9/1974 | Ropiequet |
| 3,838,692 A | 10/1974 | Levesque |
| 3,849,241 A | 11/1974 | Butin et al. |
| 3,855,046 A | 12/1974 | Hansen et al. |
| 3,857,144 A | 12/1974 | Bustin |
| 3,860,003 A | 1/1975 | Buell |
| 3,890,184 A | 6/1975 | Morgan |
| 3,904,465 A | 9/1975 | Haase et al. |
| 3,912,567 A | 10/1975 | Schwartz |
| 3,917,448 A | 11/1975 | Wood |
| 3,932,328 A | 1/1976 | Korpman |
| 3,949,128 A | 4/1976 | Ostermeier |
| 3,949,130 A | 4/1976 | Sabee et al. |
| 3,973,063 A | 8/1976 | Clayton |
| 3,978,185 A | 8/1976 | Buntin et al. |
| 3,979,050 A | 9/1976 | Cilia |
| 4,013,816 A | 3/1977 | Sabee et al. |
| 4,028,292 A | 6/1977 | Korpman |
| 4,038,346 A | 7/1977 | Feeney |
| 4,041,203 A | 8/1977 | Brock et al. |
| 4,080,348 A | 3/1978 | Korpman |
| 4,090,385 A | 5/1978 | Packard |
| 4,100,324 A | 7/1978 | Anderson et al. |
| 4,107,364 A | 8/1978 | Sisson |
| 4,148,676 A | 4/1979 | Paquette et al. |
| 4,209,563 A | 6/1980 | Sisson |
| 4,211,807 A | 7/1980 | Yazawa et al. |
| 4,239,578 A | 12/1980 | Gore |
| 4,241,123 A | 12/1980 | Shih |
| 4,248,652 A | 2/1981 | Civardi et al. |
| 4,259,220 A | 3/1981 | Bunnelle et al. |
| 4,285,998 A | 8/1981 | Thibodeau |
| 4,300,562 A | 11/1981 | Pieniak |
| 4,302,495 A | 11/1981 | Marra |
| 4,303,571 A | 12/1981 | Jansen et al. |
| 4,304,234 A | 12/1981 | Hartmann |
| 4,310,594 A | 1/1982 | Yamazaki et al. |
| 4,319,572 A | 3/1982 | Widlund et al. |
| 4,323,534 A | 4/1982 | DesMarais |
| 4,333,782 A | 6/1982 | Pieniak |
| 4,340,558 A | 7/1982 | Hendrickson |
| 4,340,563 A | 7/1982 | Appel et al. |
| 4,374,888 A | 2/1983 | Bornslaeger |
| 4,375,446 A | 3/1983 | Fujii et al. |
| 4,402,688 A | 9/1983 | Julemont |
| 4,405,397 A | 9/1983 | Teed |
| 4,413,623 A | 11/1983 | Pieniak |
| 4,417,935 A | 11/1983 | Spencer |
| 4,418,123 A | 11/1983 | Bunnelle et al. |
| 4,438,167 A | 3/1984 | Schwarz |
| 4,440,819 A | 4/1984 | Rosser et al. |
| 4,460,728 A | 7/1984 | Schmidt et al. |
| 4,490,427 A | 12/1984 | Grant et al. |
| 4,496,417 A | 1/1985 | Haake et al. |
| 4,500,316 A | 2/1985 | Damico |
| 4,507,163 A | 3/1985 | Menard |
| 4,522,863 A | 6/1985 | Keck et al. |
| 4,525,407 A | 6/1985 | Ness |
| 4,543,099 A | 9/1985 | Bunnelle et al. |
| 4,548,859 A | 10/1985 | Kline et al. |
| 4,552,795 A | 11/1985 | Hansen et al. |
| 4,555,811 A | 12/1985 | Shimalla |
| 4,572,752 A | 2/1986 | Jensen et al. |
| 4,586,199 A | 5/1986 | Birring |
| D284,036 S | 6/1986 | Birring |
| 4,606,964 A | 8/1986 | Wideman |
| 4,618,384 A | 10/1986 | Sabee |
| 4,626,305 A | 12/1986 | Suzuki et al. |
| 4,636,419 A | 1/1987 | Madsen et al. |
| 4,640,859 A | 2/1987 | Hansen et al. |
| 4,644,045 A | 2/1987 | Fowells |
| 4,652,487 A | 3/1987 | Morman |
| 4,656,081 A | 4/1987 | Ando et al. |
| 4,657,793 A | 4/1987 | Fisher |
| 4,657,802 A * | 4/1987 | Morman ..................... 428/152 |
| 4,661,389 A | 4/1987 | Mudge et al. |
| 4,663,220 A | 5/1987 | Wisneski et al. |
| 4,666,543 A | 5/1987 | Kawano |
| 4,675,068 A | 6/1987 | Lundmark |
| 4,683,877 A | 8/1987 | Ersfeld et al. |
| 4,687,477 A | 8/1987 | Suzuki et al. |
| 4,692,368 A | 9/1987 | Taylor et al. |
| 4,692,371 A | 9/1987 | Morman et al. |
| 4,698,242 A | 10/1987 | Salerno |
| 4,704,116 A | 11/1987 | Enloe |
| 4,718,901 A | 1/1988 | Singheimer |
| 4,719,261 A | 1/1988 | Bunnelle et al. |
| 4,720,415 A | 1/1988 | Vander Wielen et al. |
| 4,725,468 A | 2/1988 | McIntyre |
| 4,726,874 A | 2/1988 | VanVliet |
| 4,734,311 A | 3/1988 | Sokolowski |
| 4,734,320 A | 3/1988 | Ohira et al. |
| 4,734,447 A | 3/1988 | Hattori et al. |
| 4,735,673 A | 4/1988 | Piron |
| 4,756,942 A | 7/1988 | Aichele |
| 4,761,198 A | 8/1988 | Salerno |
| 4,762,582 A | 8/1988 | de Jonckheere |
| 4,775,579 A | 10/1988 | Hagy et al. |
| 4,777,080 A | 10/1988 | Harris, Jr. et al. |
| 4,781,966 A | 11/1988 | Taylor |
| 4,787,699 A | 11/1988 | Moulin |
| 4,789,699 A | 12/1988 | Kieffer et al. |
| 4,795,668 A | 1/1989 | Krueger et al. |
| 4,798,603 A | 1/1989 | Meyer et al. |
| 4,801,345 A | 1/1989 | Dussaud et al. |
| 4,801,482 A | 1/1989 | Goggans et al. |
| 4,803,117 A | 2/1989 | Daponte |
| 4,804,577 A | 2/1989 | Hazelton et al. |
| 4,818,464 A | 4/1989 | Lau |
| 4,818,597 A | 4/1989 | DaPonte et al. |
| 4,826,415 A | 5/1989 | Mende |
| 4,837,715 A | 6/1989 | Ungpiyakul et al. |
| 4,842,666 A | 6/1989 | Werenicz |
| 4,854,985 A | 8/1989 | Soderlund et al. |
| 4,854,989 A | 8/1989 | Singheimer |
| 4,863,779 A | 9/1989 | Daponte |
| 4,867,735 A | 9/1989 | Wogelius |
| 4,874,447 A | 10/1989 | Hazelton et al. |
| 4,883,482 A | 11/1989 | Gandrez et al. |
| 4,883,549 A | 11/1989 | Frost et al. |
| 4,891,258 A | 1/1990 | Fahrenkrug |
| 4,892,536 A | 1/1990 | DesMarais et al. |
| 4,892,903 A | 1/1990 | Himes |
| 4,900,619 A | 2/1990 | Ostrowski et al. |
| 4,906,507 A | 3/1990 | Grynaeus et al. |
| 4,908,247 A | 3/1990 | Baird et al. |
| 4,908,253 A | 3/1990 | Rasmussen |

| | | | | | | |
|---|---|---|---|---|---|---|
| 4,908,263 A | 3/1990 | Reed | | 5,312,500 A | 5/1994 | Kurihara et al. |
| 4,910,064 A | 3/1990 | Sabee | | 5,324,580 A | 6/1994 | Allan et al. |
| 4,917,696 A | 4/1990 | de Jonckheere | | 5,332,613 A | 7/1994 | Taylor et al. |
| 4,917,746 A | 4/1990 | Kons et al. | | 5,334,437 A | 8/1994 | Zafiroglu |
| 4,929,492 A | 5/1990 | Carey, Jr. et al. | | 5,334,446 A | 8/1994 | Quantrille et al. |
| 4,935,021 A | 6/1990 | Huffman et al. | | 5,336,545 A | 8/1994 | Morman |
| 4,938,757 A | 7/1990 | Van Gompel et al. | | 5,336,552 A | 8/1994 | Strack et al. |
| 4,938,821 A | 7/1990 | Soderlund et al. | | 5,342,341 A | 8/1994 | Igaue et al. |
| 4,940,464 A | 7/1990 | Van Gompel et al. | | 5,342,469 A | 8/1994 | Bodford et al. |
| 4,949,668 A | 8/1990 | Heindel et al. | | 5,360,854 A | 11/1994 | Bozich, Jr. |
| 4,965,122 A | 10/1990 | Morman | | 5,364,382 A | 11/1994 | Latimer et al. |
| 4,968,313 A | 11/1990 | Sabee | | 5,366,793 A | 11/1994 | Fitts, Jr. et al. |
| 4,970,259 A | 11/1990 | Mitchell et al. | | 5,376,198 A | 12/1994 | Fahrenkrug et al. |
| 4,977,011 A | 12/1990 | Smith | | 5,376,430 A | 12/1994 | Swenson et al. |
| 4,981,747 A | 1/1991 | Morman | | 5,382,400 A | 1/1995 | Pike et al. |
| 4,984,584 A | 1/1991 | Hansen et al. | | 5,385,775 A * | 1/1995 | Wright .......................... 442/183 |
| 4,994,508 A | 2/1991 | Shiraki et al. | | 5,389,173 A | 2/1995 | Merkatoris et al. |
| 4,995,928 A | 2/1991 | Sabee | | 5,393,599 A | 2/1995 | Quantrille et al. |
| 4,998,929 A | 3/1991 | Bjorksund et al. | | 5,399,219 A | 3/1995 | Roessler et al. |
| 5,000,806 A | 3/1991 | Merkatoris et al. | | 5,405,682 A | 4/1995 | Shawver et al. |
| 5,002,815 A | 3/1991 | Yamanaka et al. | | 5,407,507 A | 4/1995 | Ball |
| 5,005,215 A | 4/1991 | McIlquham | | 5,411,618 A | 5/1995 | Jocewicz, Jr. |
| 5,013,785 A | 5/1991 | Mizui | | 5,413,654 A | 5/1995 | Igaue et al. |
| 5,028,646 A | 7/1991 | Miller et al. | | 5,413,849 A | 5/1995 | Austin et al. |
| 5,034,008 A | 7/1991 | Breitkopf | | 5,415,644 A | 5/1995 | Enloe |
| 5,045,133 A | 9/1991 | DaPonte et al. | | 5,415,649 A | 5/1995 | Watanabe et al. |
| 5,046,272 A | 9/1991 | Vogt et al. | | 5,415,925 A | 5/1995 | Austin et al. |
| 5,057,368 A | 10/1991 | Largman et al. | | 5,422,172 A | 6/1995 | Wu |
| 5,060,349 A | 10/1991 | Walton et al. | | 5,425,987 A | 6/1995 | Shawver et al. |
| 5,069,970 A | 12/1991 | Largman et al. | | 5,429,629 A | 7/1995 | Latimer et al. |
| 5,073,436 A | 12/1991 | Antonacci et al. | | 5,429,694 A | 7/1995 | Herrmann |
| 5,093,422 A | 3/1992 | Himes | | 5,431,644 A | 7/1995 | Sipinen et al. |
| 5,096,532 A | 3/1992 | Neuwirth et al. | | 5,431,991 A | 7/1995 | Quantrille et al. |
| 5,100,435 A | 3/1992 | Onwumere | | 5,447,462 A | 9/1995 | Smith et al. |
| 5,104,116 A | 4/1992 | Pohjola | | 5,447,508 A | 9/1995 | Numano et al. |
| 5,108,820 A | 4/1992 | Kaneko et al. | | 5,449,353 A | 9/1995 | Watanabe et al. |
| 5,110,403 A | 5/1992 | Ehlert | | 5,459,186 A | 10/1995 | Gage |
| 5,112,889 A | 5/1992 | Miller et al. | | 5,464,401 A | 11/1995 | Haasse et al. |
| 5,114,087 A | 5/1992 | Fisher et al. | | 5,466,410 A | 11/1995 | Hills |
| 5,116,662 A | 5/1992 | Morman | | 5,472,775 A | 12/1995 | Obijeski et al. |
| 5,145,727 A | 9/1992 | Potts et al. | | 5,476,458 A | 12/1995 | Glaug et al. |
| 5,147,487 A | 9/1992 | Nomura et al. | | 5,476,563 A | 12/1995 | Nakata |
| 5,163,932 A | 11/1992 | Nomura et al. | | 5,484,645 A | 1/1996 | Lickfield et al. |
| D331,627 S | 12/1992 | Igaue et al. | | 5,486,166 A | 1/1996 | Bishop et al. |
| 5,169,706 A | 12/1992 | Collier, IV et al. | | 5,490,846 A | 2/1996 | Ellis et al. |
| 5,169,712 A | 12/1992 | Tapp | | 5,496,298 A | 3/1996 | Kuepper et al. |
| 5,176,668 A | 1/1993 | Bernardin | | 5,498,468 A | 3/1996 | Blaney |
| 5,176,672 A | 1/1993 | Bruemmer et al. | | 5,500,075 A | 3/1996 | Herrmann |
| 5,178,931 A | 1/1993 | Perkins et al. | | 5,501,679 A | 3/1996 | Krueger et al. |
| 5,186,779 A | 2/1993 | Tubbs | | 5,509,915 A | 4/1996 | Hanson et al. |
| 5,188,885 A | 2/1993 | Timmons et al. | | 5,514,470 A | 5/1996 | Haffner et al. |
| 5,192,606 A | 3/1993 | Proxmire et al. | | 5,516,476 A | 5/1996 | Haggard et al. |
| 5,198,281 A | 3/1993 | Muzzy et al. | | 5,523,146 A | 6/1996 | Bodford et al. |
| 5,200,246 A | 4/1993 | Sabee | | 5,527,300 A | 6/1996 | Sauer |
| 5,204,429 A | 4/1993 | Kaminsky et al. | | 5,531,850 A | 7/1996 | Herrmann |
| D335,707 S | 5/1993 | Igaue et al. | | 5,534,330 A | 7/1996 | Groshens |
| 5,209,801 A | 5/1993 | Smith | | 5,536,563 A | 7/1996 | Shah et al. |
| 5,219,633 A | 6/1993 | Sabee | | 5,540,796 A | 7/1996 | Fries |
| 5,224,405 A | 7/1993 | Pohjola | | 5,540,976 A | 7/1996 | Shawver et al. |
| 5,226,992 A | 7/1993 | Morman | | 5,543,206 A | 8/1996 | Austin et al. |
| 5,229,191 A | 7/1993 | Austin | | 5,545,158 A | 8/1996 | Jessup |
| 5,232,777 A | 8/1993 | Sipinen et al. | | 5,545,285 A | 8/1996 | Johnson |
| 5,236,430 A | 8/1993 | Bridges | | 5,549,964 A | 8/1996 | Shohji et al. |
| 5,236,770 A | 8/1993 | Assent et al. | | 5,569,232 A | 10/1996 | Roe et al. |
| 5,238,733 A | 8/1993 | Joseph et al. | | 5,575,783 A | 11/1996 | Clear et al. |
| 5,246,433 A | 9/1993 | Hasse et al. | | 5,576,090 A | 11/1996 | Suzuki |
| D340,283 S | 10/1993 | Igaue et al. | | 5,582,668 A | 12/1996 | Kling |
| 5,252,170 A | 10/1993 | Schaupp | | 5,591,152 A | 1/1997 | Buell et al. |
| 5,259,902 A | 11/1993 | Muckenfuhs | | 5,591,792 A | 1/1997 | Hattori et al. |
| 5,260,126 A | 11/1993 | Collier, IV et al. | | 5,595,618 A | 1/1997 | Fries et al. |
| 5,272,236 A | 12/1993 | Lai et al. | | 5,597,430 A | 1/1997 | Rasche |
| 5,277,976 A | 1/1994 | Hogle et al. | | 5,612,118 A | 3/1997 | Schleinz et al. |
| 5,278,272 A | 1/1994 | Lai et al. | | 5,614,276 A | 3/1997 | Petsetakis |
| 5,288,791 A | 2/1994 | Collier, IV et al. | | 5,620,780 A | 4/1997 | Krueger et al. |
| 5,290,842 A | 3/1994 | Sasaki et al. | | 5,624,740 A | 4/1997 | Nakata |
| 5,296,080 A | 3/1994 | Merkatoris et al. | | 5,626,573 A | 5/1997 | Igaue et al. |
| 5,304,599 A | 4/1994 | Himes | | 5,628,856 A | 5/1997 | Dobrin et al. |
| 5,306,545 A * | 4/1994 | Shirayanagi et al. ......... 428/198 | | 5,635,290 A * | 6/1997 | Stopper et al. ................. 428/198 |
| 5,308,345 A | 5/1994 | Herrin | | 5,645,672 A | 7/1997 | Dobrin |

| | | |
|---|---|---|
| 5,652,041 A | 7/1997 | Buerger et al. |
| 5,660,664 A | 8/1997 | Herrmann |
| 5,663,228 A | 9/1997 | Sasaki et al. |
| 5,669,897 A | 9/1997 | Lavon et al. |
| 5,674,216 A | 10/1997 | Buell et al. |
| 5,680,653 A | 10/1997 | Mathis et al. |
| 5,681,302 A | 10/1997 | Melbye et al. |
| 5,683,787 A | 11/1997 | Boich et al. |
| 5,690,626 A | 11/1997 | Suzuki et al. |
| 5,691,034 A | 11/1997 | Krueger et al. |
| 5,693,038 A | 12/1997 | Suzuki et al. |
| 5,695,849 A | 12/1997 | Shawver et al. |
| 5,702,378 A | 12/1997 | Widlund et al. |
| 5,707,709 A | 1/1998 | Blake |
| 5,709,921 A | 1/1998 | Shawver |
| 5,720,838 A | 2/1998 | Nakata |
| 5,733,635 A | 3/1998 | Terakawa et al. |
| 5,733,822 A | 3/1998 | Gessner et al. |
| 5,735,839 A | 4/1998 | Kawaguchi et al. |
| 5,736,219 A | 4/1998 | Suehr et al. |
| 5,746,731 A | 5/1998 | Hisada |
| 5,749,865 A | 5/1998 | Yamamoto et al. |
| 5,749,866 A | 5/1998 | Roe et al. |
| 5,766,389 A | 6/1998 | Brandon et al. |
| 5,766,737 A | 6/1998 | Willey et al. |
| 5,769,838 A | 6/1998 | Buell et al. |
| 5,769,993 A | 6/1998 | Baldauf |
| 5,772,649 A | 6/1998 | Siudzinski |
| 5,773,373 A | 6/1998 | Wynne et al. |
| 5,773,374 A | 6/1998 | Wood et al. |
| 5,788,804 A | 8/1998 | Horsting |
| 5,789,065 A | 8/1998 | Haffner et al. |
| 5,789,328 A | 8/1998 | Kurihara et al. |
| 5,789,474 A | 8/1998 | Lu et al. |
| 5,800,903 A | 9/1998 | Wood et al. |
| 5,804,021 A | 9/1998 | Abuto et al. |
| 5,804,286 A | 9/1998 | Quantrille et al. |
| 5,814,176 A | 9/1998 | Proulx |
| 5,814,404 A | 9/1998 | Rutherford |
| 5,817,087 A | 10/1998 | Takabayashi et al. |
| 5,818,719 A | 10/1998 | Brandon et al. |
| 5,830,203 A | 11/1998 | Suzuki et al. |
| 5,834,089 A | 11/1998 | Jones et al. |
| 5,836,931 A | 11/1998 | Toyoda et al. |
| 5,836,932 A | 11/1998 | Buell et al. |
| 5,840,412 A | 11/1998 | Wood et al. |
| 5,840,633 A | 11/1998 | Kurihara et al. |
| 5,846,232 A | 12/1998 | Serbiak et al. |
| 5,849,001 A | 12/1998 | Torimae et al. |
| 5,856,387 A | 1/1999 | Sasaki et al. |
| 5,858,515 A | 1/1999 | Stokes et al. |
| 5,860,945 A | 1/1999 | Cramer et al. |
| 5,865,933 A | 2/1999 | Morin et al. |
| 5,876,392 A | 3/1999 | Hisada |
| 5,879,776 A | 3/1999 | Nakata |
| 5,882,573 A | 3/1999 | Kwok et al. |
| 5,885,656 A | 3/1999 | Goldwasser |
| 5,885,686 A | 3/1999 | Cederblad et al. |
| 5,897,546 A | 4/1999 | Kido et al. |
| 5,899,895 A | 5/1999 | Robles et al. |
| 5,902,540 A | 5/1999 | Kwok |
| 5,904,298 A | 5/1999 | Kwok et al. |
| 5,916,206 A | 6/1999 | Otsubo et al. |
| 5,921,973 A | 7/1999 | Newkirk et al. |
| 5,930,139 A | 7/1999 | Chapdelaine et al. |
| 5,931,581 A | 8/1999 | Garberg et al. |
| 5,932,039 A | 8/1999 | Popp et al. |
| 5,941,865 A | 8/1999 | Otsubo et al. |
| D414,262 S | 9/1999 | Ashton et al. |
| 5,952,252 A | 9/1999 | Shawver et al. |
| 5,964,970 A | 10/1999 | Woolwine et al. |
| 5,964,973 A | 10/1999 | Heath et al. |
| 5,990,377 A | 11/1999 | Chen et al. |
| 5,993,433 A | 11/1999 | St. Louis et al. |
| 5,997,521 A | 12/1999 | Robles et al. |
| 6,001,460 A | 12/1999 | Morman et al. |
| 6,004,306 A | 12/1999 | Robles et al. |
| 6,009,558 A | 1/2000 | Rosch et al. |
| 6,033,502 A | 3/2000 | Coenen et al. |

| | | | |
|---|---|---|---|
| 6,045,543 A | 4/2000 | Pozniak et al. | |
| 6,048,326 A | 4/2000 | Davis et al. | |
| 6,057,024 A * | 5/2000 | Mleziva et al. | 428/114 |
| 6,066,369 A | 5/2000 | Schulz et al. | |
| 6,075,179 A * | 6/2000 | McCormack et al. | 604/367 |
| 6,087,550 A | 7/2000 | Anderson-Fischer et al. | |
| 6,090,234 A | 7/2000 | Barone et al. | |
| 6,092,002 A | 7/2000 | Kastman et al. | |
| 6,093,663 A | 7/2000 | Ouellette et al. | |
| 6,096,668 A | 8/2000 | Abuto et al. | |
| 6,123,694 A | 9/2000 | Pieniak et al. | |
| 6,132,410 A | 10/2000 | Van Gompel et al. | |
| 6,152,904 A | 11/2000 | Matthews et al. | |
| 6,169,848 B1 | 1/2001 | Henry | |
| 6,183,587 B1 | 2/2001 | McFall et al. | |
| 6,183,847 B1 | 2/2001 | Goldwasser | |
| 6,214,476 B1 | 4/2001 | Ikeda et al. | |
| 6,217,690 B1 | 4/2001 | Rajala et al. | |
| 6,231,557 B1 | 5/2001 | Krautkramer et al. | |
| 6,238,379 B1 | 5/2001 | Keuhn, Jr. et al. | |
| 6,245,050 B1 | 6/2001 | Odorzynski et al. | |
| 6,245,168 B1 | 6/2001 | Coenen et al. | |
| 6,260,211 B1 | 7/2001 | Rajala et al. | |
| 6,279,807 B1 | 8/2001 | Crowley et al. | |
| 6,290,979 B1 | 9/2001 | Roe et al. | |
| 6,310,164 B1 | 10/2001 | Morizono et al. | |
| 6,316,013 B1 | 11/2001 | Paul et al. | |
| 6,316,687 B1 | 11/2001 | Davis et al. | |
| 6,316,688 B1 | 11/2001 | Hammons et al. | |
| 6,319,865 B1 | 11/2001 | Mikami | |
| 6,320,096 B1 | 11/2001 | Inoue et al. | |
| 6,323,389 B1 | 11/2001 | Thomas et al. | |
| 6,329,459 B1 | 12/2001 | Kang et al. | |
| 6,364,863 B1 | 4/2002 | Yamamoto et al. | |
| 6,365,659 B1 | 4/2002 | Aoyama et al. | |
| 6,475,600 B1 | 11/2002 | Morman et al. | |
| 6,503,855 B1 | 1/2003 | Menzies | |
| 6,537,935 B1 | 3/2003 | Seth et al. | |
| 6,645,190 B1 | 11/2003 | Olson et al. | |
| 6,649,548 B1 | 11/2003 | Shawver et al. | |
| 6,657,009 B2 | 12/2003 | Zhou | |
| 6,774,069 B2 | 8/2004 | Zhou | |
| 6,803,009 B2 | 10/2004 | Morman | |
| 6,872,784 B2 | 3/2005 | Zhou | |
| 6,902,796 B2 | 6/2005 | Morell | |
| 6,909,028 B1 | 6/2005 | Shawver et al. | |
| 6,939,334 B2 | 9/2005 | Odorzynski | |
| 2002/0002021 A1 | 1/2002 | May et al. | |
| 2002/0009940 A1 | 1/2002 | May et al. | |
| 2002/0019616 A1 | 2/2002 | Thomas | |
| 2002/0081423 A1 | 6/2002 | Heffelfinger | |
| 2002/0104608 A1 | 8/2002 | Welch et al. | |
| 2002/0122953 A1 | 9/2002 | Zhou | |
| 2002/0123538 A1 | 9/2002 | Zhou et al. | |
| 2002/0123726 A1 | 9/2002 | Zhou et al. | |
| 2002/0138063 A1 | 9/2002 | Kuen et al. | |
| 2002/0153086 A1 | 10/2002 | Alper et al. | |
| 2002/0164465 A1 | 11/2002 | Curro et al. | |
| 2003/0065297 A1 | 4/2003 | Davis | |
| 2003/0091807 A1 | 5/2003 | Desai et al. | |
| 2003/0096896 A1 | 5/2003 | Wang et al. | |
| 2003/0232928 A1 | 12/2003 | Atwood et al. | |
| 2004/0127128 A1 | 7/2004 | Thomas | |
| 2005/0054779 A1 | 3/2005 | Zhou | |

FOREIGN PATENT DOCUMENTS

| | | |
|---|---|---|
| DE | 34 23 644 | 1/1986 |
| DE | 37 34 963 | 4/1988 |
| EP | 0 155 636 | 9/1985 |
| EP | 0 172 037 | 2/1986 |
| EP | 0 217 032 | 4/1987 |
| EP | 0 239 080 | 9/1987 |
| EP | 0 330 716 | 9/1989 |
| EP | 0341870 | 11/1989 |
| EP | 0 380 781 | 8/1990 |
| EP | 0 396 800 | 11/1990 |
| EP | 0 456 885 | 11/1991 |
| EP | 0 547 497 | 6/1993 |
| EP | 0 548 609 | 6/1993 |

| | | |
|---|---|---|
| EP | 0 582 569 | 2/1994 |
| EP | 0 604 731 | 7/1994 |
| EP | 0 617 939 | 10/1994 |
| EP | 0 688 550 | 12/1995 |
| EP | 0 689 815 | 1/1996 |
| EP | 0 713 546 | 5/1996 |
| EP | 0 743 052 | 11/1996 |
| EP | 0 753 292 | 1/1997 |
| EP | 0 761 193 | 3/1997 |
| EP | 0 761 194 | 3/1997 |
| EP | 0 763 353 | 3/1997 |
| EP | 0 787 474 | 8/1997 |
| EP | 0 802 251 | 10/1997 |
| EP | 0 806 196 | 11/1997 |
| EP | 0 814 189 | 12/1997 |
| EP | 0 873 738 | 10/1998 |
| EP | 0 888 101 | 1/1999 |
| EP | 0 901 780 | 3/1999 |
| EP | 1 013 251 | 6/2000 |
| EP | 1298240 | 4/2003 |
| GB | 2 244 422 | 12/1991 |
| GB | 2 250 921 | 6/1992 |
| GB | 2 253 131 | 9/1992 |
| GB | 2 267 024 | 11/1993 |
| GB | 2 268 389 | 1/1994 |
| IL | 092891 | 2/1992 |
| JP | 3-67646 | 3/1991 |
| JP | 2003113574 * | 4/2003 |
| WO | WO 80/00676 | 4/1980 |
| WO | WO 90/03464 | 4/1990 |
| WO | WO 91/07277 | 5/1991 |
| WO | WO 92/16364 | 10/1992 |
| WO | WO 92/16371 | 10/1992 |
| WO | WO 93/15247 | 8/1993 |
| WO | WO 93/17648 | 9/1993 |
| WO | WO 94/09736 | 5/1994 |
| WO | WO 95/03443 | 2/1995 |
| WO | WO 95/04182 | 2/1995 |
| WO | WO 95/16425 | 6/1995 |
| WO | WO 95/16562 | 6/1995 |
| WO | WO 95/34264 | 12/1995 |
| WO | WO 96/13989 | 5/1996 |
| WO | WO 96/23466 | 8/1996 |
| WO | WO 96/35402 | 11/1996 |
| WO | WO 97/17046 | 5/1997 |
| WO | WO 98/14156 | 4/1998 |
| WO | WO 98/49988 | 11/1998 |
| WO | WO 98/55062 | 12/1998 |
| WO | WO 99/17926 | 4/1999 |
| WO | WO 99/24519 | 5/1999 |
| WO | WO 99/47088 | 9/1999 |
| WO | WO 99/47590 | 9/1999 |
| WO | WO 9947088 * | 9/1999 |
| WO | WO9947088 * | 9/1999 |
| WO | WO 99/60969 | 12/1999 |
| WO | WO 99/60970 | 12/1999 |
| WO | WO 99/60971 | 12/1999 |
| WO | WO 00/10500 | 3/2000 |
| WO | WO 00/29199 | 5/2000 |
| WO | WO 00/37003 | 6/2000 |
| WO | WO 00/37005 | 6/2000 |
| WO | WO 00/37009 | 6/2000 |
| WO | WO 00/37723 | 6/2000 |
| WO | WO 00/59429 | 10/2000 |
| WO | WO 01/00053 | 1/2001 |
| WO | WO 01/32116 | 5/2001 |
| WO | WO 01/45617 | 6/2001 |
| WO | WO 01/49907 | 7/2001 |
| WO | WO 01/87214 | 11/2001 |
| WO | WO 02/34184 | 5/2002 |
| WO | WO 02/34512 | 5/2002 |
| WO | WO 02/060690 | 8/2002 |
| WO | WO 02/085624 | 10/2002 |
| WO | WO 2005/065932 | 7/2005 |

OTHER PUBLICATIONS

Yorkgitis, "Adhesive Compounds", Encyclopedia of Polymer Science and Technology, Online Posting Date Mar. 15, 2002.*
Wente et al., *Manufacture of Superfine Organic Fibers*, NRL Report 4364, U.S. Naval Research Laboratory, (May 1954) (19 pages).
Lawrence et al., *An Improved Device for the Formation of Superfine, Thermoplastic Fibers*, NRL Report 5265, U.S. Naval Research Laboratory (Feb. 1959) (9 pages).

* cited by examiner

SINGLE SIDED STRETCH BONDED LAMINATES, AND METHODS OF MAKING SAME

RELATED APPLICATION

This application is a continuation-in-part of U.S. patent application Ser. No. 10/750,295, filed 31 Dec. 2003 now U.S Pat. No. 7,601,657. The disclosure of the prior application is incorporated herein by reference.

FIELD OF THE INVENTION

The present invention relates to continuous filament and film-based stretch bonded laminate materials for use on or in various personal care products, and other products requiring stretch capability, and manufacturing methods for making such stretch bonded laminate materials.

BACKGROUND OF THE INVENTION

The term "stretch bonded laminate" refers to a composite elastic material made according to a stretch bonding lamination process, i.e., elastic layer(s) are joined together with additional facing layers when only the elastic layer is in an extended condition (such as by at least about 25 percent of its relaxed length) so that upon relaxation of the layers, the additional layer(s) is/are gathered. Such laminates usually have machine directional (MD) stretch properties and may be subsequently stretched to the extent that the additional (typically non-elastic) material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 5,385,775 to Wright and copending U.S. Patent Publication No. 2002-0104608, published 8 Aug. 2002, each of which is incorporated by reference herein in its entirety. Such stretch bonded laminates may include an elastic component that is a web, such as a meltblown web, a film, an array/series of generally parallel continuous filament strands (either extruded or pre-formed), or a combination of such. The elastic layer is bonded in a stretched condition to two inelastic or extendable nonwoven facing materials, such that the resulting laminate is imparted with a textural feel that is pleasing on the hand. In particular, the elastic layer is bonded between the two facing layers, such that the facing layers sandwich the elastic layer. In some instances, the gatherable facing layers may also be necked, such that the stretch bonded laminate is actually a necked stretch bonded laminate that may have some extension/elasticity in the cross-machine direction (CD).

To "neck" or "necked" refers to a process of tensioning a fabric in a particular direction thereby reducing the width dimension of the fabric in the direction perpendicular to the direction of tension. For example, tensioning a nonwoven fabric in the MD causes the fabric to "neck" or narrow in the CD and give the necked fabric CD stretchability. Examples of such extensible and/or elastic fabrics include, but are not limited to, those described in U.S. Pat. No. 4,965,122 to Morman et al. and U.S. Pat. No. 5,336,545 to Morman et al. each of which is incorporated herein by reference in its entirety.

"Neck bonding" refers to the process wherein an elastic member is bonded to a non-elastic member while only the non-elastic member is extended or necked so as to reduce its dimension in the direction orthogonal to the extension. "Neck bonded laminate" refers to a composite elastic material made according to the neck bonding process, i.e., the layers are joined together when only the non-elastic layer is in an extended/necked condition. Such laminates usually have cross directional stretch properties. Further examples of neck-bonded laminates are such as those described in U.S. Pat. Nos. 5,226,992, 4,981,747 to Morman and U.S. Pat. No. 5,514,470 to Haffner et al., each of which is incorporated by reference herein in its entirety.

"Neck-stretch bonding" generally refers to a process wherein an elastic member is bonded to another member while the elastic member is extended (such as by about 25 percent of its relaxed length) and the other layer is a necked, non-elastic layer. "Neck-stretch bonded laminate" refers to a composite elastic material made according to the neck-stretch bonding process, i.e., the layers are joined together when both layers are in an extended condition and then allowed to relax. Such laminates usually have multi-directional stretch properties.

Such stretch bonded laminates may be used to provide elasticity to various components of a personal care product and with the added benefit of a pleasant fabric-like touch, such as a diaper liner or outercover, diaper waist band material, diaper leg gasketing (cuff) material, diaper ear portions (that is, the point of attachment of a fastening system to a diaper), as well as side panel materials for diapers and child training pants. Since such materials often come in contact with skin of a human body, it is desirable that such materials be relatively soft to the touch, rather than rubbery in their feel (a sensation common for elastic materials). Such materials may likewise provide elasticity and comfort for materials that are incorporated into protective workwear, such as surgical gowns, face masks and drapes, labcoats, or protective outercovers, such as car, grill or boat covers.

While such soft and stretchy materials have assisted in making such elastic materials more user-friendly, there is still a need for such products that provide even more of a cloth-like fabric feel. In this regard, there is a need for such materials that provide even higher levels of gathering. Further, there is a need for such laminate products with even greater flexibility as a result of reduced overall basis weight. There is likewise a need for a laminate material that provides reduced stiffness as a result of the elimination of one facing layer on the laminate and the use of lower basis weight elastic layer components. Such a laminate would be more efficient in its use as an elastic material, plus the elimination of one facing layer would be cost-effective. Such a laminate could provide ease of use/extension, with better ability to retract since there would be no drag of extra facing layers. Essentially, such a laminate would provide for higher levels of retraction with lower weights of polymer. However, even with all of these perceived benefits, to date a single sided stretch bonded laminate (that is a stretch bonded laminate with a gatherable facing layer on only one side) has been elusive because of manufacturing challenges.

In utilizing stretch bonded laminates that themselves incorporate an adhesive component, it has been desirable to select adhesives that do not add to the stiffness of the material. Such stiffness has a negative impact on the overall feel of the product and the ability of the product to provide stretch attributes when in use. It therefore would be desirable to develop additional adhesive arrangements that would not negatively impact laminate material feel and performance, while still allowing for the formation of a single sided material.

Many adhesives are typically somewhat elastic themselves, and tend to retain some level of tackiness even after they are dried or cured. As a result, because of their inherent tackiness, it has been necessary, at least with respect to filament, film, and web based stretch bonded laminates, to utilize facings on both sides of the center elastic component (i.e. filament array), so as to avoid roll blocking during processing/ storage. For the purposes of this application, the terms "roll blocking" and "roll sticking" shall be used interchangeably, and shall refer to the propensity of tacky films, tacky filament arrays or other tacky sheet materials to stick to themselves upon being rolled up for storage, prior to final use. Such roll blocking may prevent use of the material contained on a roll as a result of the inability to unwind such rolled material when it is actually needed. In filament-based stretch bonded laminates, adhesive is often applied to the facing layers themselves, and then the facing layers are combined in a nip with the filament array between them. Such an arrangement may generally be described as an ABA laminate, where A is a facing layer and B is an elastic layer.

While it would be desirable to reduce the basis weight of the stretch bonded laminate such that the material is less costly and more flexible, it has been heretofore unclear how to eliminate the extra facing layer(s) without causing the rolled material to stick, if it is to be stored prior to use. It is therefore desirable to have a single sided stretch-bonded laminate that demonstrates acceptable elastic performance, but that is also capable of being stored on a roll without concern for roll blocking. It is also desirable to have a material that may be maintained on a roll under acceptable storage conditions, such as for a given period of time, and at a range of temperatures. It is to such needs that the current invention is directed.

SUMMARY OF THE INVENTION

An elastic laminate capable of being rolled for storage, and unwound from a roll when needed for use, includes an elastic layer of an array of continuous filament strands with meltblown deposited on the continuous filament strands, and a facing layer bonded to only one side of the elastic layer. The elastic laminate includes an elastic polyolefin-based polymer having a degree of crystallinity between about 3% and about 40%, or between about 5% and about 30%. The elastic polyolefin-based polymer may have a melt flow rate between about 10 and about 600 grams per 10 minutes, or between about 60 and about 300 grams per 10 minutes, or between about 150 and about 200 grams per 10 minutes; a melting/ softening point between about 40 and about 160 degrees Celsius; and/or a density from about 0.8 to about 0.95, or about 0.85 to about 0.93, or about 0.86 to about 0.89 grams per cubic centimeter. The elastic polyolefin-based polymer may include polyethylene, polypropylene, butene, or octene homo- or copolymers, ethylene methacrylate, ethylene vinyl acetate, butyl acrylate copolymers, or a combination of any of these polymers. The elastic polyolefin-based polymer may be used to form the meltblown layer, the continuous filament strands, and/or the facing layer.

The elastic laminate may further include an adhesive that demonstrates a relatively short open time deposited between the array of continuous filament strands and the meltblown layer, or between the elastic layer and the gatherable facing layer. In certain embodiments, the elastic laminate may include a nonblocking agent layer deposited on the elastic layer, on a side opposite to the facing layer; however, a nonblocking agent layer is not necessary when the meltblown layer includes the elastic polyolefin-based polymer.

More particularly, when the meltblown layer includes the elastic polyolefin-based polymer, the elastic laminate suitably has an inter-layer peel strength of less than about 70 grams per 3 inches cross-directional width at a strain rate of 300 millimeters/minute (mm/min). For example, when the elastic laminate is rolled upon itself, it can be unwound for future use and demonstrates a peel strength from a roll (while it is being unwound) of less than about 70 grams per 3 inches cross-directional width at a strain rate of 300 mm/min. In yet another alternative embodiment, such elastic laminate demonstrates a peel strength from a roll of less than about 60 grams per 3 inches cross-directional width at a strain rate of 300 mm/min. In yet another alternate embodiment, such elastic laminate demonstrates a peel strength from a roll of less than about 50 grams per 3 inches cross-directional width at a strain rate of 300 mm/min. Thus, the elastic laminate may not require any post-calender treatment such as a nonblocking agent or the like.

In still a further alternative embodiment, the elastic laminate includes an adhesive between the array of continuous filament strands and the meltblown layer, or between the facing layer and the elastic layer, that demonstrates an open time of between about 0.2 seconds and 1 minute, or between about 0.2 seconds and 3 seconds, or between about 0.5 seconds and 2 seconds. In still another alternative embodiment, such elastic laminate includes an adhesive between the array of continuous filament strands and the meltblown layer, or between the facing layer and the elastic layer, wherein the adhesive is applied in an amount less than about 16 gsm, or less than about 8 gsm, or less than about 4 gsm, or between about 1 and 4 gsm. In still another alternative embodiment, the laminate includes an adhesive between the facing layer and the elastic layer, and also on a side of the elastic layer opposite to that of the facing layer. In still a further alternative embodiment, such adhesive is distributed in similar add-on amounts between the facing layer and the elastic layer and also to the side of the elastic layer opposite to that of the facing layer.

The meltblown layer in the elastic layer may be a single layer of meltblown material or, alternatively, may include two or more layers. For example, one of the layers may include an elastic polyolefin-based meltblown polymer having a degree of crystallinity between about 3% and about 40%, or between about 5% and about 30%, and another layer may include a styrenic block copolymer-based meltblown polymer.

The meltblown layer may be present within the elastic laminate at an add-on up to about 34 grams per square meter (gsm), or between about 1 and about 5 gsm, or between about 1.25 and about 2.5 gsm, at the point of lamination.

In still another alternative embodiment of the invention, the elastic layer has an overall basis weight up to about 54 gsm. In still another alternative embodiment of the invention, the elastic layer has a basis weight of between about 4 gsm and 23 gsm, or between about 10 gsm and 18 gsm.

In still another alternative embodiment of the invention, the facing layer has a basis weight of between about 0.3 and 1.5 osy. In yet another alternative embodiment of the invention, the facing layer is selected from the group consisting of nonwoven webs, nonwoven web laminates, foams, scrims, netting, films, and combinations thereof. In yet another embodiment of the invention, the single gatherable facing layer is necked. In certain embodiments, the facing layer may include a spunbond-meltblown-spunbond laminate in which the meltblown layer includes an elastic polyolefin-based polymer and is positioned between two spunbond layers.

In yet another alternative embodiment of the invention, an extensible facing layer is bonded to an elastic or semi-elastic film having a basis weight of about 50 grams per square meter (gsm) or less, or between about 35 to about 45 gsm, or between about 38 and about 42 gsm. The film and/or the facing layer(s) may include an elastic polyolefin-based polymer as described herein. The laminate displays greater retraction than comparable laminates having two conventional facing layers. The laminate may also include elastomeric strands. As a further alternative, the laminate may include a second extensible facing layer bonded to the opposite surface of the film.

In an alternative embodiment, a method for forming a stretch bonded laminate includes forming an elastic layer by applying an elastic meltblown polymer to an array of continuous filament strands; stretching the elastic layer; bonding a gatherable facing layer to the stretched elastic layer adjacent to the meltblown layer while the stretched elastic layer is in a stretched condition, to form a stretch bonded laminate; and allowing such stretched bonded laminate to retract. A single side facing stretch bonded laminate (which term shall be used synonymously with single sided stretch bonded laminate) made by the method, for use in a personal care or other stretchable article is also contemplated by the invention.

In another alternative embodiment, a method for forming a single facing stretch bonded laminate includes providing an elastic layer; applying a meltblown nonblocking agent to one side of the elastic layer; stretching the elastic layer; bonding a gatherable facing layer only to the stretched elastic layer on a side opposite to the meltblown nonblocking agent while the stretched elastic layer is in a stretched condition, to form a single sided stretch bonded laminate; and allowing such stretched bonded laminate to retract.

In a further alternative embodiment, a method for forming a single sided stretch bonded laminate includes providing an elastic layer; stretching the elastic layer; bonding a gatherable facing layer to only one side of the stretched elastic layer while the stretched elastic layer is in a stretched condition to form a stretch bonded laminate by using an adhesive with a relatively short open time, and that is not tacky following curing; and allowing such stretched bonded laminate to retract. In still a further alternative embodiment, the adhesive is applied to bond the elastic layer to the single gatherable facing layer both prior to contacting the elastic layer with the facing layer (prebonding adhesive application) and following contacting the elastic layer with the facing layer (postbonding application). The prebonding adhesive application is applied prior to the elastic layer and facing layer being brought together into a laminate. In one embodiment, the postbonding adhesive application is applied to the filament side of the laminate, after the elastic layer and facing layer have been laminated. In a further alternative embodiment, similar amounts of adhesive are applied in both the prebonding and postbonding adhesive applications. It is contemplated that the invention also includes a single sided stretch bonded laminate made by such adhesive methods and articles made from such laminates.

BRIEF DESCRIPTION OF THE DRAWINGS

The invention will be better understood by reference to the following description of embodiments of the invention taken in conjunction with the accompanying drawings, wherein.

DEFINITIONS

Within the context of this specification, each term or phrase below will include the following meaning or meanings.

Figure 7:
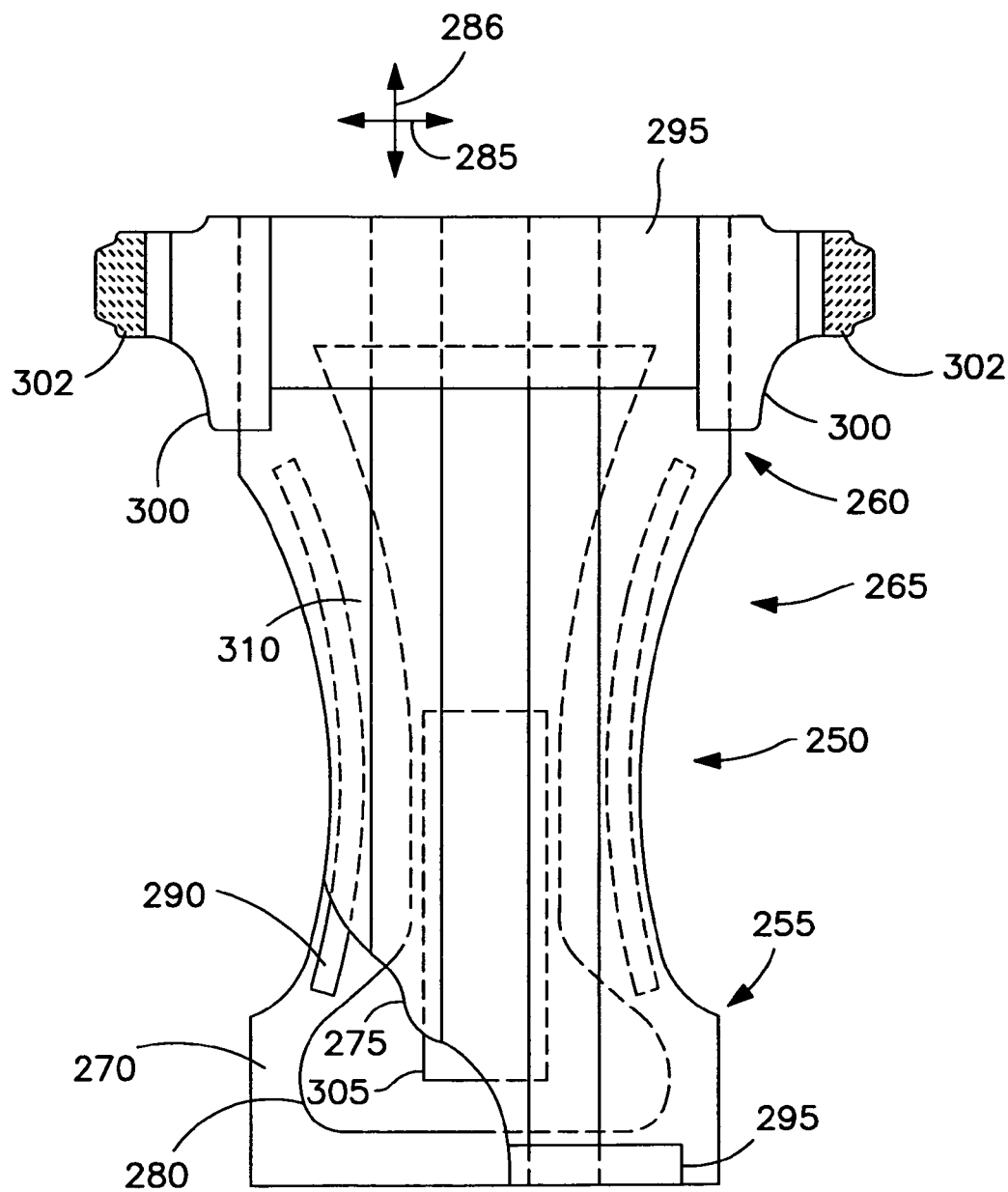
FIG. 7 illustrates a personal care product utilizing a single sided stretch bonded laminate made in accordance with the invention.

As used herein, the term "personal care product" means diapers, training pants, swimwear, absorbent underpants, adult incontinence products, and feminine hygiene products, such as feminine care pads, napkins and pantiliners. While a diaper is illustrated in FIG. 7, it should be recognized that the inventive material may just as easily be incorporated in any of the previously listed personal care products as an elastic component. For instance, such material may be utilized to make the elastic side panels of training pants.

As used herein the term "protective outerwear" means garments used for protection in the workplace, such as surgical gowns, hospital gowns, covergowns, labcoats, masks, and protective coveralls.

As used herein, the terms "protective cover" and "protective outercover" mean covers that are used to protect objects such as for example car, boat and barbeque grill covers, as well as agricultural fabrics.

As used herein, the terms "polymer" and "polymeric" when used without descriptive modifiers, generally include but are not limited to, homopolymers, copolymers, such as for example, block, graft, random and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic and random symmetries.

As used herein, the terms "machine direction" or MD means the direction along the length of a fabric in the direction in which it is produced. The terms "cross machine direction," "cross directional," or CD mean the direction across the width of fabric, i.e. a direction generally perpendicular to the MD.

As used herein, the term "nonwoven web" means a polymeric web having a structure of individual fibers or threads which are interlaid, but not in an identifiable, repeating manner. Nonwoven webs have been, in the past, formed by a variety of processes such as, for example, meltblowing processes, spunbonding processes, hydroentangling, air-laid and bonded carded web processes.

As used herein, the term "bonded carded webs" refers to webs that are made from staple fibers which are usually purchased in bales. The bales are placed in a fiberizing unit/picker which separates the fibers. Next, the fibers are sent through a combining or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern through the web and/or alternatively the web may be bonded across its entire surface if so desired. When using bicomponent staple fibers, through-air bonding equipment is, for many applications, especially advantageous.

As used herein the term "spunbond" refers to small diameter fibers which are formed by extruding molten thermoplastic material as filaments from a plurality of fine, usually circular capillaries of a spinneret with the diameter of the extruded filaments being rapidly reduced as by means shown, for example in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and U.S. Pat. No. 3,341,394 to Kinney, U.S. Pat. No. 3,542,615 to Dobo et al., each of which is incorporated by reference in its entirety herein.

As used herein, the term "meltblown" means fibers formed by extruding a molten thermoplastic material through a plurality of fine, usually circular die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; and U.S. Pat. No. 3,849,241, issued Nov. 19, 1974, to Butin, et al. incorporated by reference herein in its entirety.

As used herein, the terms "sheet" and "sheet material" shall be interchangeable and in the absence of a word modifier, refer to woven materials, nonwoven webs, polymeric films, polymeric scrim-like materials, and polymeric foam sheeting.

The basis weight of nonwoven fabrics or films is usually expressed in ounces of material per square yard (osy) or grams per square meter (g/m² or gsm) and the fiber diameters are usually expressed in microns. (Note that to convert from osy to gsm, multiply osy by 33.91). Film thicknesses may also be expressed in microns or mil.

As used herein, the term "laminate" refers to a composite structure of two or more sheet material layers that have been adhered through a bonding step, such as through adhesive bonding, thermal bonding, point bonding, pressure bonding, extrusion coating or ultrasonic bonding.

As used herein, the term "elastomeric" shall be interchangeable with the term "elastic" and refers to sheet material which, upon application of a stretching force, is stretchable in at least one direction (such as the CD direction), and which upon release of the stretching force contracts/returns to approximately its original dimension. For example, a stretched material having a stretched length which is at least 50 percent greater than its relaxed unstretched length, and which will recover to within at least 50 percent of its stretched length upon release of the stretching force. A hypothetical example would be a one (1) inch sample of a material which is stretchable to at least 1.50 inches and which, upon release of the stretching force, will recover to a length of not more than 1.25 inches. Desirably, such elastomeric sheet contracts or recovers up to 50 percent of the stretch length in a particular direction, such as in either the machine direction or the cross machine direction. Even more desirably, such elastomeric sheet material recovers up to 80 percent of the stretch length in a particular direction, such as in either the machine direction or the cross machine direction. Even more desirably, such elastomeric sheet material recovers greater than 80 percent of the stretch length in a particular direction, such as in either the machine direction or the cross machine direction. Desirably, such elastomeric sheet is stretchable and recoverable in both the MD and CD directions.

As used herein, the term "semi-elastic" refers to sheet material that may be elastic or elastomeric, or that may be stretchable in at least one direction (such as the CD direction) and upon release of the stretching force at least partially retracts. For example, when a semi-elastic material is stretched to 200% its original dimension, upon release of the stretching force, the semi-elastic material will retract to less than 200% its original dimension, such as less than 175% its original dimension, or less than 150% its original dimension.

As used herein, the term "elastomer" shall refer to a polymer which is elastomeric.

As used herein, the term "thermoplastic" shall refer to a polymer which is capable of being melt processed.

As used herein, the term "inelastic" or "nonelastic" refers to any material which does not fall within the definition of "elastic" above.

As used herein, the term "multilayer laminate" means a laminate including a variety of different sheet materials. For instance, a multilayer laminate may include some layers of spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al., and U.S. Pat. No. 5,188,885 to Timmons et al., each incorporated by reference herein in its entirety. Such a laminate may be made by sequentially depositing onto a moving forming belt first a spunbond fabric layer, then a meltblown fabric layer and last another spunbond layer and then bonding the laminate, such as by thermal point bonding. Alternatively, the fabric layers may be made individually, collected in rolls, and combined in a separate bonding step or steps. Multilayer laminates may also have various numbers of meltblown layers or multiple spunbond layers in many different configurations and may include other materials like films (F) or coform materials, e.g. SMMS, SM, SFS.

As used herein, the term "coform" means a process in which at least one meltblown diehead is arranged near a chute through which other materials are added to the web while it is forming. Such other materials may be pulp, superabsorbent particles, cellulose or staple fibers, for example. Coform processes are shown in U.S. Pat. No. 4,818,464 to Lau and U.S. Pat. No. 4,100,324 to Anderson et al., each incorporated by reference herein in its entirety.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side-by-side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. No. 5,069,970 and U.S. Pat. No. 5,057,368 to Largman et al., which describe fibers with unconventional shapes. Each of the foregoing patents is incorporated by reference herein in its entirety.

As used herein the term "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for finctional as well as aesthetic reasons. One example of a pattern has points and is the Hansen Pennings or "H&P" pattern with about a 30 percent bond area with about 200 bonds/square inch as taught in U.S. Pat. No. 3,855,046 to Hansen and Pennings, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5 percent. Another typical point bonding pattern is the expanded Hansen Pennings or "EHP" bond pattern which produces a 15 percent bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15 percent. Yet another common pattern is the C-Star pattern which has a bond area of about 16.9 percent. The C-Star pattern has a cross-directional bar or "corduroy" design interrupted by shooting stars. Other common patterns include a diamond pattern with repeating and slightly offset diamonds with about a 16 percent bond area and a wire weave pattern looking as the name suggests, e.g. like a window screen pattern having a bond area in the range of from about 15 percent to about 21 percent and about 302 bonds per square inch.

Typically, the percent bonding area varies from around 10 percent to around 30 percent of the area of the fabric laminate. As is well known in the art, the spot bonding holds the laminate layers together as well as imparts integrity to each individual layer by bonding filaments and/or fibers within each layer.

As used herein, the term "ultrasonic bonding" means a process performed, for example, by passing the fabric between a sonic horn and anvil roll as illustrated in U.S. Pat. No. 4,374,888 to Bornslaeger, incorporated by reference herein in its entirety.

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein, the term "post-calender treatment" refers to any treatment, such as the application of a nonblocking agent, that is typically applied to a laminate toward the end of the lamination process, such as following the passage of the laminate through a nip or over a calender roll, in order to reduce inter-layer peel strength.

As used herein, the term "inter-layer peel strength" refers to the peel strength required to separate a laminate from itself when unwound from a roll, as opposed to the peel strength between layers within the laminate. Inter-layer peel strength can be determined using the Roll Blocking Test Method described in detail below.

As used herein, and in the claims, the term "comprising" is inclusive or open-ended and does not exclude additional unrecited elements, compositional components, or method steps. Accordingly, such term is intended to be synonymous with the words "has", "have", "having", "includes", "including", and any derivatives of these words.

As used herein, the terms "extensible" or "expandable" mean elongatable in at least one direction, but not necessarily recoverable.

Unless otherwise indicated, percentages of components in formulations are by weight.

DETAILED DESCRIPTION OF THE INVENTION

For the purposes of this invention an elastic single sided stretch bonded laminate includes at least one elastic layer and one gatherable facing layer, the gatherable facing layer being applied to only one side of at least one elastic layer. The elastic layer suitably includes an array of continuous filament strands with a meltblown layer deposited on the continuous filament strands. The laminate suitably includes an elastic polyolefin-based polymer having a degree of crystallinity between about 3% and about 40%, or between about 5% and about 30%, or between about 15% and about 25%. The elastic polyolefin-based polymer may also have a melt flow rate between about 10 and about 600 grams per 10 minutes, or between about 60 and about 300 grams per 10 minutes, or between about 150 and about 200 grams per 10 minutes; a melting/softening point between about 40 and about 160 degrees Celsius; and/or a density from about 0.8 to about 0.95, or about 0.85 to about 0.93, or about 0.86 to about 0.89 grams per cubic centimeter. The elastic polyolefin-based polymer may include polyethylene, polypropylene, butene, or octene homo- or copolymers, ethylene methacrylate, ethylene vinyl acetate, butyl acrylate copolymers, or a combination of any of these polymers.

One example of a suitable elastic polyolefin-based polymer is VISTAMAXX, available from ExxonMobil Chemical of Baytown, Tex. Other examples of suitable polyolefin-based polymers include EXACT plastomer, OPTEMA ethylene methacrylate, and VISTANEX polyisobutylene, and metallocene-catalyzed polyethylene, all available from ExxonMobil Chemical, as well as AFFINITY polyolefin plastomers, such as AFFINITY EG8185 or AFFINITY GA1950, available from Dow Chemical Company of Midland, Mich.; ELVAX ethylene vinyl acetate, available from E. I. Du Pont de Nemours and Company of Wilmington, Del.; and ESCORENE Ultra ethylene vinyl acetate, available from ExxonMobil.

The elastic polyolefin-based polymer suitably has a slow crystallization rate, with partial regions of crystalline and amorphous phases that make it inherently elastic and tacky.

The elastic polyolefin-based polymer may be incorporated within the meltblown layer, the continuous filament strands, and/or the facing layer, as described in greater detail below.

It is desirable that such single-sided stretch bonded laminate material demonstrate a stretch to stop value of between about 30 and 400 percent. In an alternative embodiment, such material demonstrates a stretch to stop value of between about 50 and 300 percent. In still a further alternative embodiment, such laminate material demonstrates a stretch to stop value of between about 80 and 250 percent.

As mentioned, the elastic layer suitably includes an array of continuous filament strands with a meltblown layer deposited on the continuous filament strands. Additional components may be included in the elastic layer, such as a film, an elastic scrim or netting structure, a foam material, or a combination of any of the foregoing materials. If a film is used, it may be an apertured film. In certain embodiments, any of these additional components may be used in place of the array of continuous filament strands and/or the meltblown layer. The combination of a generally parallel series of elastomeric continuous filaments or strands (fiber array) and meltblown materials deposited on the filaments is described in previously noted U.S. Pat. No. 5,385,775 to Wright. The filament to meltblown basis weight ratio in such an elastic layer may be about 90:10, for example.

At least one of the components of the elastic layer may be formed from an elastic polyolefin-based polymer having a degree of crystallinity between about 3% and about 40%, or between about 5% and about 30%, or between about 15% and about 25%, as described above. When the elastic polymer is used to form the meltblown layer, for example, the slow crystallization rate of the elastic polymer is advantageous because the meltblown fibers are semi-tacky as they are deposited on the forming wire, which keeps the elastic strands in place and adhesively bonds the composite. Additionally, when the meltblown layer includes the elastic polymer, the meltblown layer may be applied at a higher add-on compared to non-elastic meltblown layers. More particularly, the elastic meltblown layer may be applied at an add-on up to about 34 gsm, or between about 1 and about 5 grams per square meter (gsm), or between about 1.25 and about 2.5 gsm, as measured when the layer is fully extended. Inelastic meltblown tends to crack and form discrete islands as the strands stretch prior to lamination at higher add-on levels, which leads to non-uniformity. However, elastic meltblown does not suffer such drawbacks at higher add-on levels. Furthermore, the higher add-on of elastic meltblown coupled with the tackiness of the elastic meltblown helps to better secure the filaments to the facing layer such that the filaments are less likely to come loose, as demonstrated by inter-layer peel strength that is greater than intra-layer peel strength. More particularly, the peel strength of the layers within the laminate is greater than the peel strength of the exterior surfaces of the layers to one another when the laminate is unwound from a roll. For instance, the laminate may have an intra-layer peel strength of about 200 to about 450 grams per 3 inches cross-directional width at a strain rate of 300 mm/min, using the same test method as used for determining the inter-layer peel strength but instead pulling apart the elastic layer from the facing layer. The higher add-on of elastic meltblown may also help reduce porosity.

Another benefit of using the elastic polyolefin-based polymer in the meltblown layer is the reduction or elimination of roll blocking, as demonstrated through the low inter-layer peel strength of the laminate. Other laminates may include post-calender treatment, such as non-elastic polypropylene meltblown dusting, to prevent roll blocking, but the incorporation of the elastic polymer in the meltblown layer may remove the need for any post-calender treatment. Incorporation of the elastic meltblown layer without any post-calender treatment may result in an inter-layer peel strength of the laminate of less than about 70 grams per 3 inches cross-directional width at a strain rate of 300 mm/min, or less than about 60 grams per 3 inches cross-directional width at a strain rate of 300 mm/min, or less than about 50 grams per 3 inches cross-directional width at a strain rate of 300 mm/min. A shorter width of laminate may provide non-uniform results, but for the most part the inter-layer peel strength of the laminate has a linear relationship with respect to the width of the laminate. Thus, for example, a laminate having a width of 3 inches may exhibit inter-layer peel strength of about 60 grams per 3 inches cross-directional width at a strain rate of 300 mm/min, while the same laminate having a width of 1 inch may exhibit inter-layer peel strength of about 20 grams per inch cross-directional width at a strain rate of 300 mm/min.

Figure 8:
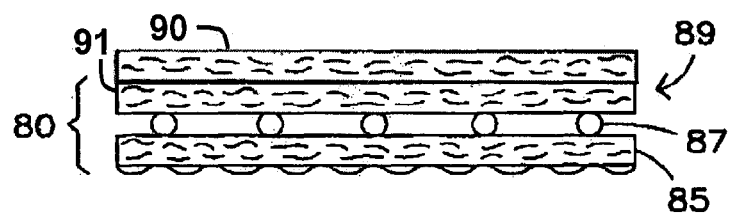
FIG. 8 illustrates a cross-sectional view of an embodiment of a single sided stretch bonded laminate with a multi-layer meltblown layer.

The meltblown layer may include, for example, between about 30% and about 100%, or between about 50% and about 80%, by weight elastic polyolefin-based polymer. The meltblown layer may be a single layer or a multi-layer component, as shown in FIG. 8. For example, the meltblown layer may include a layer of an elastic polyolefin-based meltblown polymer 90 having a degree of crystallinity between about 3% and about 40% and the meltblown layer may also include a layer of styrenic block copolymer-based meltblown polymer 91, as described in greater detail below.

As mentioned, the continuous filament strands may also include an elastic polyolefin-based polymer. More particularly, the continuous filament strands may be composed of between about 5% and about 90%, or between about 30% and about 70%, by weight elastic polyolefin-based polymer.

Furthermore, any or all of the components within the elastic layer (whether the meltblown layer, the filaments, or other components) may include thermoplastic materials such as block copolymers having the general formula A-B-A' where A and A' are each a thermoplastic polymer endblock which contains a styrenic moiety such as a poly (vinyl arene) and where B is an elastomeric polymer midblock such as a conjugated diene or a lower alkene polymer.

Specific examples of useful styrenic block copolymers include hydrogenated polyisoprene polymers such as styrene-ethylenepropylene-styrene (SEPS), styrene-ethylenepropylene-styrene-ethylenepropylene (SEPSEP), hydrogenated polybutadiene polymers such as styrene-ethylenebutylene-styrene (SEBS), styrene-ethylenebutylene-styrene-ethylenebutylene (SEBSEB), styrene-butadiene-styrene (SBS), styrene-isoprene-styrene (SIS), and hydrogenated poly-isoprene/butadiene polymer such as styrene-ethylene-ethylenepropylene-styrene (SEEPS). Polymer block configurations such as diblock, triblock, multiblock, star and radial are also contemplated in this invention. In some instances, higher molecular weight block copolymers may be desirable. Block copolymers are available from Kraton Polymers U.S. LLC of Houston, Tex. under the designations Kraton G or D polymers, for example G1652, G1657, G1730, D1114, D1155, D1102 and Septon Company of America, Pasadena, Tex. under the designations Septon 2004, Septon 4030, and Septon 4033. Other potential suppliers of such polymers include Dexco Polymers of Tex. and Dynasol of Spain. Blends of such elastomeric resin materials are also contemplated as the primary component of the elastic layer. Additionally, other desirable block copolymers are disclosed in U.S. Patent Publication 2003/0232928A1 which is incorporated by reference herein in its entirety.

Such base resins may be further combined with tackifiers and/or processing aids in compounds. Exemplary compounds include but are not limited to KRATON G 2760, and KRATON G 2755. Processing aids that may be added to the elastomeric polymer described above include a polyolefin to improve the processability of the composition. The polyolefin must be one which, when so blended and subjected to an appropriate combination of elevated pressure and elevated temperature conditions, is extrudable, in blended form, with the elastomeric base polymer. Useful blending polyolefin materials include, for example, polyethylene, polypropylene and polybutene, including ethylene copolymers, propylene copolymers and butene copolymers. A particularly useful polyethylene may be obtained from Eastman Chemical under the designation EPOLENE C-10. Two or more of the polyolefins may also be utilized. Extrudable blends of elastomeric polymers and polyolefins are disclosed in, for example, U.S. Pat. No 4,663,220.

The elastomeric filaments may have some tackiness/adhesiveness to enhance autogenous bonding. For example, the elastomeric polymer itself may be tacky when formed into films, and/or filaments or, alternatively, a compatible tackifying resin may be added to the extrudable elastomeric compositions described above to provide tackified elastomeric fibers and/or filaments that autogenously bond. In regards to the tackifying resins and tackified extrudable elastomeric compositions, note the resins and compositions as disclosed in U.S. Pat. No.4,787,699, hereby incorporated by reference in its entirety.

Any tackifier resin can be used which is compatible with the elastomeric polymer and can withstand the high processing (e.g. extrusion) temperatures. If the elastomeric polymer (e.g. A-B-A elastomeric block copolymer) is blended with processing aids such as, for example, polyolefins or extending oils, the tackifier resin should also be compatible with those processing aids. Generally, hydrogenated hydrocarbon resins are preferred tackifying resins, because of their better temperature stability. REGALREZ series tackifiers are examples of such hydrogenated hydrocarbon resins. REGALREZ hydrocarbon resins are available from Eastman Chemical. Of course, the present invention is not limited to use of such tackifying resins, and other tackifying resins which are compatible with the other components of the composition and can withstand the high processing temperatures, can also be used. Other tackifiers are available from ExxonMobil under the ESCOREZ designation.

Other exemplary elastomeric materials which may be used include polyurethane elastomeric materials such as, for example, those available under the trademark ESTANE from Noveon, polyamide elastomeric materials such as, for example, those available under the trademark PEBAX (polyether amide) from Ato Fina Company, and polyester elastomeric materials such as, for example, those available under the trade designation HYTREL from E. I. DuPont De Nemours & Company.

Useful elastomeric polymers also include, for example, elastic polymers and copolymers of ethylene and at least one vinyl monomer such as, for example, vinyl acetates, unsaturated aliphatic monocarboxylic acids, and esters of such monocarboxylic acids. The elastic copolymers and formation of elastomeric meltblown fibers from those elastic copolymers are disclosed in, for example, U.S. Pat. No. 4,803,117, incorporated by reference herein in its entirety.

Additional materials which may be utilized in the elastic layer to provide some extensibility with limited recovery, include single site catalyzed polyolefinic materials, such as metallocene catalyzed polyolefins and constrained geometry polyolefins, as available from Dow under the designation AFFINITY and from ExxonMobil, under the designation EXACT. Desirably, such materials have densities of less than 0.89 g/cc.

Finally, pre-formed elastic strands are also contemplated to be within the scope of this invention. Such preformed strands, such as solution treated materials, include LYCRA from Dupont and GLOSPAN, available from GLOBE. This material may serve as the basis for a continuous filament array component (elastic layer) of a stretch bonded laminate material, or alternatively a film component of a stretch bonded laminate.

Typically, the blend used to form the web, film or filaments when such is made from an extruded material in an on-line process, includes for example, from about 40 to about 90 percent by weight elastomeric polymer base resin, from about 0 to about 40 percent polyolefin processing aid, and from about 5 to about 40 percent resin tackifier. These ratios can be varied depending on the specific properties desired and the polymers utilized. For an alternative embodiment, such blend includes between about 60 and 80 percent base resin, between about 5 to 30 percent processing aid, and between about 10 and 30 percent tackifier. In a further alternative embodiment, such blend includes a tackifier in an amount of between about 10 and 20 percent tackifier.

In embodiments in which the meltblown layer does not include the elastic polyolefin-based polymer, a nonblocking agent may be applied to the elastic layer either as a nonblocking agent layer on a side opposite to that of the facing layer, or as a bonding agent (adhesive) between the elastic layer and the gatherable facing layer, or alternatively, as a bonding agent between the elastic layer and the gatherable facing layer and additionally over the bonded laminate, on a side opposite to that of the facing layer.

The gatherable facing layer gathers between points on its surface that are bonded to the elastic layer. Essentially, those areas that are gathered are not bonded to the elastic layer. While it is desirable that the gatherable layer be a nonwoven layer, such gatherable layer may also be a woven web, a cellulosic web as will later be described, a metallic foil-type layer or a combination of such. Such gatherable material may also be pretreated in some fashion prior to being bonded to the elastic layer. Such pretreatments include for instance being necked. Such pretreatment may offer additional properties to the overall laminate material, such as bi or multidirectional stretch capabilities. Such gatherable layer may itself include multiple layers, and as such be a multilayered laminate.

The gatherable facing layer may be a nonwoven material such as, for example, one or more spunbonded webs (such as a conjugate fiber spunbond web), meltblown webs, or bonded carded webs. An example of a spunbond web may be a polypropylene spunbond web having a basis weight of between about 0.3 and 0.8 osy. In a further alternative embodiment, the spunbond web is necked between about 25 and 60 percent before it is bonded to the elastic layer. In still a further embodiment of the invention, the gatherable layer is a multilayer material having, for example, at least one layer of spunbond web joined to at least one layer of meltblown web, bonded carded web, or other suitable material. The gatherable layer may also be a composite material made of a mixture of two or more different fibers or a mixture of fibers and particulates, such as a coform material. Such mixtures may be formed by adding fibers and/or particulates to the gas stream in which meltblown fibers are carried so that an intimate entangled comingling of meltblown fibers and other materials, i.e. woodpulp, staplefibers and particulates such as, for example, hydrocolloid (hydrogel), particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference in its entirety. The facing layer may either be unwound from a roll or formed in-line.

Figure 2:
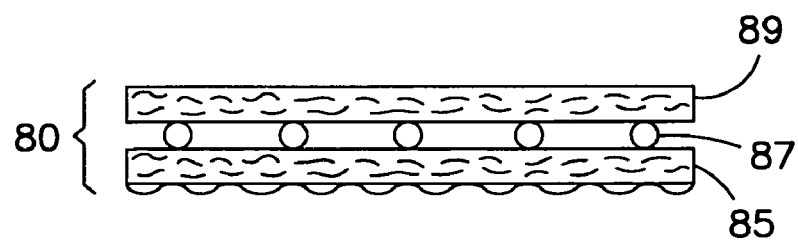
FIG. 2 illustrates a cross sectional view of one embodiment of a single sided stretch bonded laminate material.

As mentioned, the facing layer may also include an elastic polyolefin-based polymer, as described above. More particularly, the facing layer may be composed of between about 0% and about 100%, or between about 60% and about 100%, by weight elastic polyolefin-based polymer. In certain embodiments, for example, the facing layer may be a spunbond-meltblown-spunbond laminate in which the meltblown layer includes, in whole or in part, the -elastic polyolefin-based polymer. Alternatively, the facing layer may be spunbond, meltblown, hydroentangled, or other type of nonwoven material including the elastic polyolefin-based polymer. In certain embodiments, for example, both the facing layer and the elastic meltblown layer may include an elastic polyolefin-based polymer, as described above. In such embodiments, the laminate does not include any conventional facing layers per se, but instead may include two layers of the elastic polyolefin-based polymer positioned on opposite sides of the array of continuous filament strands. More particularly, as illustrated in FIG. 2, both the facing layer 85 and the meltblown layer 89 may include the elastic polyolefin-based polymer.

The gatherable layer may be made of pulp fibers, including wood pulp fibers, to form a material such as, for example, a tissue layer. Additionally, the gatherable layer may be a layer or layers of hydraulically entangled fibers such as, for example hydraulically entangled mixtures of wood pulp and staple fibers such as disclosed, for example, in U.S. Pat. No. 4,781,966, the disclosure of which is hereby incorporated by reference in its entirety.

The single sided stretch bonded laminate is desirably made using one of three methods. In particular, the material may be made using either an extrusion and bonding method with an elastic polyolefin-based meltblown layer having a slow rate of crystallization, or an extrusion and bonding method with a meltblown nonblocking agent treatment thereon (to form a nonblocking agent layer), an application of a pre-bonding adhesive that has a relatively low open time and becomes non-tacky following application, or an application of a pre-bonding adhesive that has a relatively low open time and a post-bonding application of such an adhesive, with the adhesive becoming non-tacky following application. The various methods may be described in one embodiment as involving a bonding agent, even though all of the methods do not involve "adhesives" per se. The methods can be variously characterized as involving mechanical entanglement which, in effect, mechanically bonds layers together without a tacky result.

The attributes of a semi-tacky elastic polyolefin-based meltblown layer having a slow rate of crystallization are described above. More particularly, the meltblown fibers are semi-tacky when deposited on the forming wire, which keeps the elastic strands in place and adhesively bonds the laminate. Additionally, the elastic meltblown layer can be applied at a relatively high add-on, which contributes to the bonding between the facing layer and the filaments.

In embodiments including a nonblocking agent, the nonblocking agent treatment may include application of a relatively low basis weight meltblown material, such that no readily visible (with the human eye) web is formed, to the top of tacky elastic layers within the laminate. Such nonblocking agent treatment is desirably a dusting of meltblown, such as between about 0.2 and 2.0 gsm of meltblown materials. In an alternative embodiment, such meltblown application is between about 0.2 and 1.5 gsm of meltblown materials. In still another alternative embodiment, such meltblown application is between about 0.2 and 0.8 gsm. In yet another alternative embodiment, such meltblown application is between about 0.2 and 0.5 gsm. The basis weight of the meltblown materials is determined at the point of lamination. Depending on what attributes are desired, the meltblown application is varied within these respective ranges. For instance, if a more elastic laminate is desired, the meltblown application would necessarily be on the lower end of the range. Desirably, such meltblown is a non-tacky polypropylene meltblown material which is exemplified by VALTEC HH442H (having a MFR of 1100 at 230° C./2.16 kg of ASTM D1238) by Basell, and Basell PF-015. Such meltblown material may be produced by one or more meltblown banks depending on the basis weight desired. Alternatively, such meltblown may be of an elastic material without tackifier.

If an adhesive method is used to create such single sided facing stretch bonded laminate, it is desirable that such adhesive have a relatively short open time of between about 0.2 seconds (sec) and 1 minute. In an alternative embodiment, such open time is between about 0.2 sec and 3 seconds. In still a further alternative embodiment, such open time is between about 0.5 sec and 2 seconds. An exemplary adhesive with such properties is a polypropylene-based hot melt adhesive (that becomes nontacky shortly after application, upon solidification) consisting of up to 65 percent or between about 15-40 percent atactic polypropylene, in one embodiment about 50 weight percent Huntsman H2115 (atactic polypropylene from Huntsman Polymers); between about 20-50 percent tackifier, in one embodiment about 30 percent ExxonMobil ESCOREZ 5300; between about 2-10 percent styrenic block copolymer, in one embodiment about 4 percent SEPTON 2002 of Septon Polymers; between about 10-20 percent isotactic polypropylene, in one embodiment, about 16 percent PP 3746G (isotactic polypropylene) also of ExxonMobil; between about 0-2 percent coloring agent, in one embodiment about 2 percent of a coloring agent, such as 50 percent titanium dioxide in VECTOR 4411 and finally; between about 0.2-1 percent stabilizer, in one embodiment, about 0.5 percent IRGANOX 1010 from Ciba Specialty Chemicals. It should be appreciated that the various components may have other substitutes, such as stabilizers other than IRGANOX. Furthermore, it should be appreciated that such adhesives may also not contain coloring agents, depending on product application. Other adhesives may be used with the present invention including those derived from the adhesives described in U.S. Pat. Nos. 6,657,009 and 6,774,069, U.S. application Ser. Nos. 09/945,239, 09/945,240, 10/655,717, and U.S. Publication Nos. US20020122953, US20020123726, each of which is incorporated herein by reference in its entirety.

In one embodiment, it is desirable that the adhesive be applied in a pre-bonding step (that is prior to (such as immediately prior to) bringing the elastic layer and the single facing layer together in a nip) at a basis weight of less than about 16 gsm. In an alternative embodiment, such adhesive is applied at a basis weight of less than about 8 gsm. In still a further alternative embodiment, it is desirable that such adhesive be applied at a basis weight of less than about 4 gsm. In still a further alternative embodiment, it is desirable that the adhesive be applied at between 1 and 4 gsm. In one embodiment, it is desirable that such adhesive be applied by spray, such as through systems available from ITW or other such spray applications. Such spray application is in one embodiment sprayed onto one of the layers, such as on the facing layer or the meltblown layer. In an alternative embodiment, such spray is into the nip at which the facing and elastic layers are joined, or at which the meltblown layer and the filaments are joined.

If the adhesive is to be applied as a pre-bonding and post-bonding step (prebonding as previously described), it is desirable that the adhesive be applied on the materials (as will be described below) in an amount of less than 4 gsm prior to bonding of the various layers. In an alternative embodiment, such adhesive is desirably applied in an amount of less than 2 gsm prior to bonding of the various layers. In still another alternative embodiment, such adhesive is applied in a prebonding step in a range of between about 1 and 4 gsm and in a post bonding step of between about 0-4 gsm. In still a further alternative embodiment, such adhesive is applied in a prebonding and post bonding method at a total of between about 6 and 8 gsm. The term postbonding refers to a post-calender treatment and, more specifically, shall mean application of the adhesive or nonblocking agent following exiting of the bonded elastic layer and facing layer from a nip, and before winding on a roll for storage. For example, application of the postbonding adhesive or nonblocking agent can be to a side of the elastic layer/facing layer laminate opposite to the facing layer.

In one embodiment, a method for producing a single sided facing stretch bonded elastic laminate material utilizes a facing such as that which has been previously described, and an array of continuous elastic filaments bonded to the facing through the application of the elastic meltblown layer, such that the laminate has a structure of ABC, in which the "A" represents the single side facing, the "B" represents the elastic meltblown layer, and the "C" represents the continuous elastic filaments. Alternatively, the "B" may represent the continuous elastic filaments and the "C" may represent the elastic meltblown layer. In such a fashion the resulting material demonstrates increased stretch levels, and the ability of the material to be rolled for storage over itself if it is not to be used immediately. The material likewise demonstrates enhanced gathering of the single facing since the stretch bonded laminate is allowed to retract to a greater extent than would be possible with two opposing facing layers attached.

Figure 1:
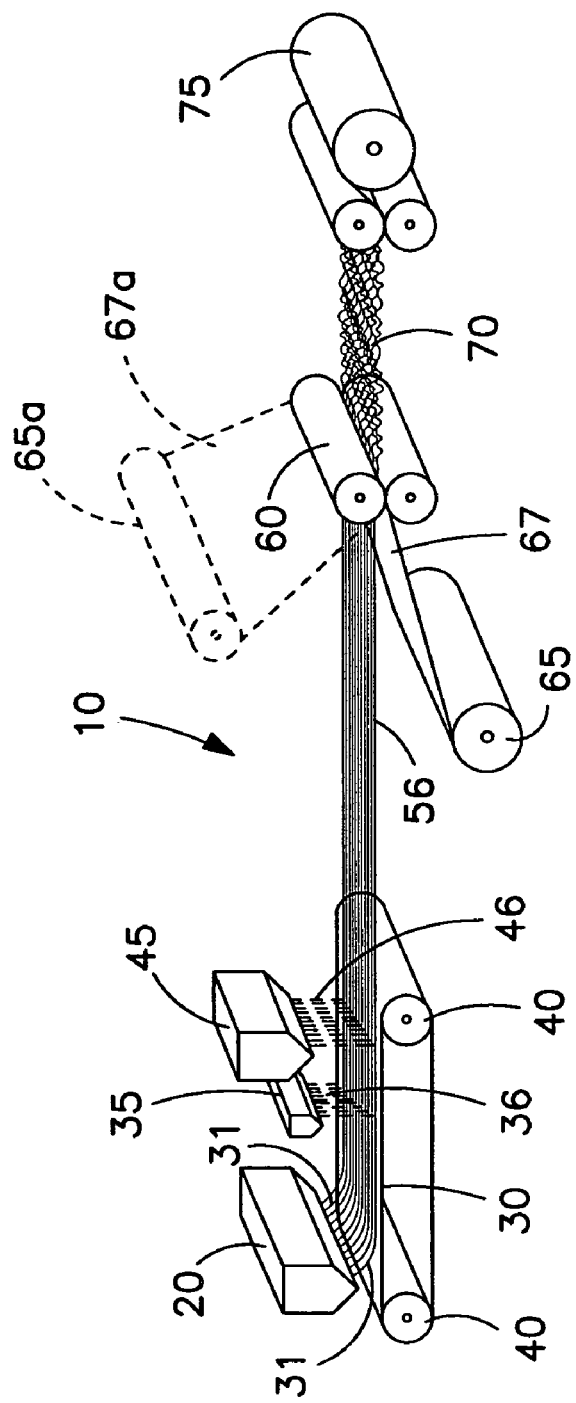
FIG. 1 illustrates a method of manufacturing a single sided stretch bonded laminate in accordance with the invention.

As can be seen in FIG. 1, which illustrates a schematic view of a method for manufacturing a single sided stretch bonded laminate material in accordance with the invention, FIG. 1 illustrates a horizontal, continuous filament laminate manufacturing process 10. A first extrusion apparatus 20 is fed with a polymer blend composition from one or more sources (not shown) which is extruded onto a forming surface 30 in filament form 31. The extruded polymer is desirably a styrenic block copolymer elastomer and/or an elastic polyolefin-based polymer. In various embodiments, the extrusion apparatus 20, or a second extrusion apparatus 35, can be configured to produce other materials, e.g. thermoplastic fibers 36, to achieve the inline placement of layers of the same or different materials. Techniques for fiber extrusion, such as modified meltblowing of the fibers, are further set forth in the previously mentioned U.S. Pat. No. 5,385,775 to Wright. Apparatus 20 extrudes filaments 31 directly onto a conveyor system, which can be a forming surface system 30 (e.g., a foraminous belt) moving clockwise about rollers 40. A vacuum (not shown) can also help hold the filaments 31 against the foraminous wire system. A meltblown layer, also of an elastomeric material such as the materials previously described, particularly an elastic polyolefin-based polymer, is extruded from adjacent bank 45, such that the meltblown fibers 46 are placed on top of the continuous filaments 31 (array). The meltblown material is in one embodiment applied such that it represents 10 basis weight percent of the filament and meltblown structure, for example. In a particular embodiment, the elastic polyolefin-based polymer composition is the same in both the filaments and meltblown materials. In an alternative embodiment, the compositions are different (which may include the same base resin, but different percentages of processing aid or tackifiers).

In certain embodiments, particularly those wherein the meltblown layer does not include an elastic polyolefin-based polymer, one or more additional meltblown banks (not shown) may be positioned downstream and adjacent the first meltblown bank to extrude a nonblocking agent onto the top of the extruded elastic meltblown layer(s). Such a nonblocking agent may be a polyolefin or elastic polyolefin polymer as previously described. Additionally, amorphous polyalpha olefins (APAO) that are non tacky may be utilized. Additionally, elastomeric materials without tackifiers may also be utilized. In a further alternative embodiment polypropylene adhesives such as previously described may likewise be meltblown on top of the previous elastic meltblown material. In melting the materials, a grid melter (typical hot melt equipment) may be used to melt/provide inorganic or organic drums, pellets, or blocks of nonblocking agent.

The filament/meltblown laminate may be stretched by the differential speed of tensioning rollers (nip rolls) 60 to elongate and tension the filaments 56. Optionally, the laminate may be compacted, and tensioned, by an additional pair of rolls (not shown). The tension rollers are therefore operating at speeds which exceed the speed at which the meltblown covered filament array is exiting the forming surface. Desirably the tension rollers 60 are provided with a surface having little to no affinity for the filaments or fibers. In one embodiment, the filaments are stretched between about 3 and 6× from the forming surface to the tensioning rollers.

At the same time, a single facing layer 67 is either made in line or unwound from a roll 65 and introduced into the set of nip rolls 60 with the filament array laminate such that the facing layer 67 faces the filament array side of the laminate, as opposed to the meltblown side of the laminate. Alternatively, the single facing layer 67a may be introduced into the set of nip rolls 60 with the filament array laminate such that the facing layer 67a faces the meltblown side of the laminate, as opposed to the filament array side of the laminate, as shown in dashed lines in FIG. 1.

The facing is bonded to the elastic layer (meltblown in particular, via pressure in the nip) while the elastic layer is still being stretched. Both the filament array and facing then exit the nip 60 as a continuous filament elastic stretch bonded laminate with a single side facing layer. The elastic laminate 70 is then allowed to relax, forming gathers therein between bonding points on the facing layer, and is collected on a collection roll 75 for further use. The collection roll then winds the laminate, typically at a speed less than that of the nip rolls, such as between about 0.50 and 0.75 of the nip roll speeds. The nip rollers 60 may be desirably designed to provide a 100 percent bond area through the use of flat calender rolls or may provide a patterned bond area. The rollers 60 can be heated to a degree below the melting/softening points of the various laminate components, or may be ambient, or chilled. As an alternative embodiment of the method, all rolls that come into contact with the non-facing side of the laminate desirably include a non-stick surface, such as a coating of PTFE (TEFLON), or silicone rubber, release coating. Such rolls may further be coated with IMPREGLON coatings of Southwest Impreglon, of Houston, Tex., or Stowe-Woodward Silfex silicone rubber coatings of a hardness of 60 Shore A. In an alternative embodiment of this continuous filament array laminate method, rather than extruding continuous filaments, preformed elastic strands such as LYCRA strands may be unwound from a drum and fed into a laminating nip under tension. In still another embodiment, the facing can be necked prior to being bonded to the elastic layer. Such necking may be between about 25 and 60 percent.

Figure 3:
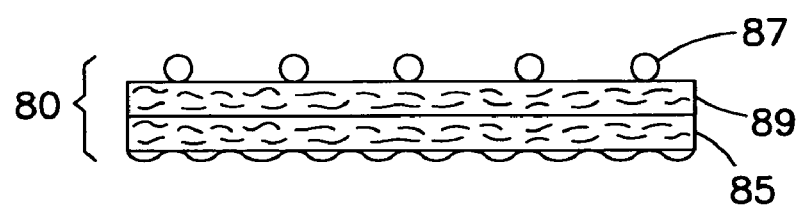
FIG. 3 illustrates a cross sectional view of another embodiment of a single sided stretch bonded laminate material.

Such laminate structure can be seen in FIG. 2 which illustrates a cross sectional stylistic view of a laminate 80 made in accordance with the invention. As can be seen in the figure, the facing 85 may be situated under/immediately adjacent the filament array 87. An elastic meltblown layer 89 is positioned on top of the filament array 87 on a side opposite to that of the facing layer 85. Alternatively, as illustrated in cross section in FIG. 3, a laminate 80 made in accordance with the invention may include the facing 85 situated under/immediately adjacent the elastic meltblown layer 89, with the filament array 87 on top of the meltblown layer 89 on a side opposite to that of the facing layer 85. The thicknesses of the various layers are not to scale, and are exaggerated to illustrate their existence. It should be recognized that while each of the various cross sections of these figures illustrate a relatively flat facing layer material, such nonwoven facing layer materials are actually gathered between where they are bonded to the respective elastic layers (either the strands, film, or webs), but for stylistic purposes, such web is shown in a relatively flat configuration. If desired, such single sided filament laminate may then be bonded to additional sheet materials as previously described.

In one embodiment, the continuous filaments in such laminates are desirably present in an amount between about 7 to 18, or about 8 to 15 per cross-directional inch. The basis weight of the meltblown material from the first elastic meltblown bank may be up to about 34 gsm, or between about 1 and 5 gsm, at the point of lamination. The basis weight of such facing materials bonded to such filaments is desirably between about 0.3 and 0.8 osy. In one embodiment, the filament and elastic meltblown materials are stretched between approximately 50 and 800 percent by the action of the nip rolls (expressed in a ratio, such as about 0.16 to 0.18 (forming surface speed/nip roll speed)). In a second alternative embodiment, the filaments are stretched between about 100 and 600 percent by the action of the nip rolls.

As an example of this embodiment of the invention, an ABC structure laminate may be produced in accordance with the methods of U.S. Pat. No. 5,385,775, with a polypropylene spunbond facing having a basis weight between about 0.3 and 0.6 osy, but desirably in the range of about 0.35 to 0.4 osy. The elastic components B and C, which desirably comprise the filament array and the elastic meltblown layer, desirably include an elastic polyolefin-based polymer, such as VISTAMAXX available from ExxonMobil. Desirably, such polymeric blend also includes a KRATON G polymeric compounded blend such as KRATON G 2760 or KRATON G 2755 in the filaments, and either the same polymeric blend in the elastic meltblown layer or a second G polymer blend in the meltblown layer. The filaments to meltblown weight ratio may be in a 90:10 ratio, or other suitable ratio.

Figure 4:
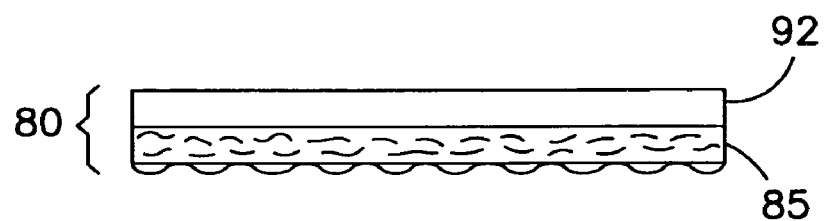
FIG. 4 illustrates a cross sectional view of yet another embodiment of a single sided stretch bonded laminate material.

In certain embodiments, an extensible or semi-elastic facing layer 85 is bonded to an elastic or semi-elastic film 92 having a basis weight of about 50 grams per square meter (gsm) or less, or between about 35 to about 45 gsm, or between about 38 and about 42 gsm, as illustrated in FIG. 4. The facing layer 85 is lower in extension tension than the film 92. Consequently, the laminate 80 displays greater retraction than comparable laminates having two conventional facing layers. This substantial amount of elastic recovery may be attributable to the reinforcing, material mass, and distribution of the extensible or semi-elastic facing layer 85. More particularly, because the force required to cause permanent deformation of the facing layer 85 is not exceeded, an increase in recovery force is possible. Furthermore, when stretched, these laminates perform as a mono-component material instead of a multi-component constructed laminate.

Figure 5:
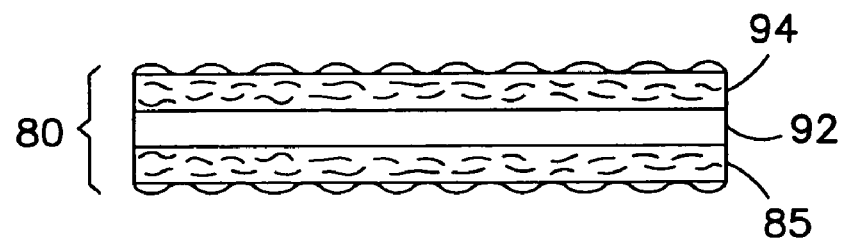
FIG. 5 illustrates a cross sectional view of one embodiment of a double sided stretch bonded laminate material.

The extensible or semi-elastic facing layer 85 may include the elastic polyolefin-based polymer, described in detail above, and may be meltblown, spunbond, hydroentangled, or any other type of nonwoven material, also described in detail above. Furthermore, the laminate 80 may include a second extensible facing layer 94, the same as or different than the first facing layer 85 bonded to a surface of the film 92 opposite the first facing layer 85, as illustrated in FIG. 5. The laminate 80 may also include a plurality of elastomeric strands, if desired. The incorporation of the elastic polyolefin-based polymer into one or more facing layers aids in the reduction of extension force and permits the use of a lower basis weight elastic or semi-elastic film. Additionally or alternatively, the film 92 may include an elastic polyolefin-based polymer. Examples of other suitable film materials include any of the elastomeric polymers described herein, particularly those described with respect to the elastic layer in previous embodiments, provided the film has a basis weight of about 50 gsm or less, or between about 35 to about 45 gsm, or between about 38 and about 42 gsm.

In manufacturing the material for examples, the following conditions were employed. The first extrusion bank that extruded continuous filaments, extruded KRATON G2760 at 26 lbs/hr. The stretch-to-stop (rSTS) of the filaments for each sample is indicated in Table 1. The elastic meltblown bank, which followed the filament bank downstream, extruded either BASELL PF-015 polypropylene/nonblocking agent, or VISTAMAXX 2210 (VM) elastic polyolefin-based polymer available from ExxonMobil, at either a low (2.5 gsm) or high (4.9 gsm) add-on. The wire to calender speed ratio was between 0.17 and 0.19, inclusive. When an adhesive was used, the adhesive add-on was 1.5 gsm at the nip. The meltblown pounds per inch per hour (PIH) is the rate at which the polymer was applied in the CD across the width of the filament die, and is indicated in Table 1 for each applicable sample.

The extrusion temperature of the continuous filament extrusion die system was between about 440 and 500° F. There was no primary air on this continuous filament system and the polymer was extruded out onto the forming wire from the filament die. The extrusion temperature of the elastic meltblown layer that was placed on top of the filaments was 451° F. The primary air in the elastic meltblown bank was between about 0.8 and 1 psi at about 475° F. The extrusion temperature of the nonblocking agent meltblown die system was between about 350 and 500° F., with the die itself having a temperature of about 450° F. The primary air in that die was about 0.8 to 1 psi. The facing basis weight, which was a polypropylene spunbond nonwoven, was 0.4 osy. The facing was unwound near the stretch zone and laminated with the meltblown and strand composite. The materials were calendered in a nip with the calender rolls yielding a surface temperature of ambient to 70 to 85° F. and under a pressure of about 250 pounds per linear inch on the roll. The entire laminate was allowed to retract and wound onto a 3-inch core.

The materials were produced having the composition and manufacturing results as reflected in Table 1 below. The materials were slabbed off of each roll and cut into 4-inch by 6-inch samples and then put in a hydraulic press overnight to simulate forces in the roll. The Roll Blocking Test Method, described in detail below, was used at a 180 degree angle at room temperature to determine inter-layer peel strength and to quantify blocking potential. One sample of each laminate was tested in 10 repetitions, and the average was converted from grams per 4-inch width to grams per 3-inch width based on the essentially linear relationship between the inter-layer peel strength and the width of the roll.

TABLE 1

| Sample | RSTS | MB Add-on (gsm) | MB Type | Winder (fpm) | MB PIH | Adh. (RPM) | Inter-Layer Peel Strength (grams per 3-inch width) |
|---|---|---|---|---|---|---|---|
| 1 | 60 | 2.5 | PF-015 | 94 | NA | NA | 126 |
| 2 | 60 | 2.5 | PF-015 | 94 | NA | 8.3 | 170 |
| 3 | 120 | 4.9 | PF-015 | 74 | NA | 6.6 | 116 |
| 4 | 120 | 4.9 | PF-015 | 74 | NA | NA | 155 |
| 5 | 60 | 4.9 | VM | 94 | 0.75 | 6.6 | 35 |
| 6 | 120 | 4.9 | VM | 74 | 0.75 | 6.6 | 47 |
| 7 | 60 | 4.9 | VM | 94 | 0.75 | NA | 14 |
| 8 | 120 | 4.9 | VM | 74 | 0.75 | NA | 13 |
| 9 | 60 | 2.5 | VM | 94 | 0.38 | NA | 29 |
| 10 | 120 | 2.5 | VM | 74 | 0.38 | 6.6 | 47 |
| 11 | 120 | 4.9 | VM | 74 | 0.75 | 6.6 | 47 |
| 12 | 60 | 2.5 | VM | 94 | 0.38 | 8.3 | 47 |

The test data provided in Table 1 indicates the elastic meltblown facing using VISTAMAXX does not roll block. More particularly, the VISTAMAXX samples had significantly lower inter-layer peel strength, around 13-47 grams per 3-inch width versus 116-170 grams per 3-inch width without VISTAMAXX. This demonstrates that samples made with VISTAMAXX have less probability of roll blocking.

In a second alternative embodiment of a method for making a single side facing stretch bonded laminate, a vertical oriented extrusion platform may be used to extrude an elastic continuous filament array. In this embodiment, a non-tacky adhesive bonding method may be employed to bond the elastic continuous filament array to the facing material.

Figure 6:
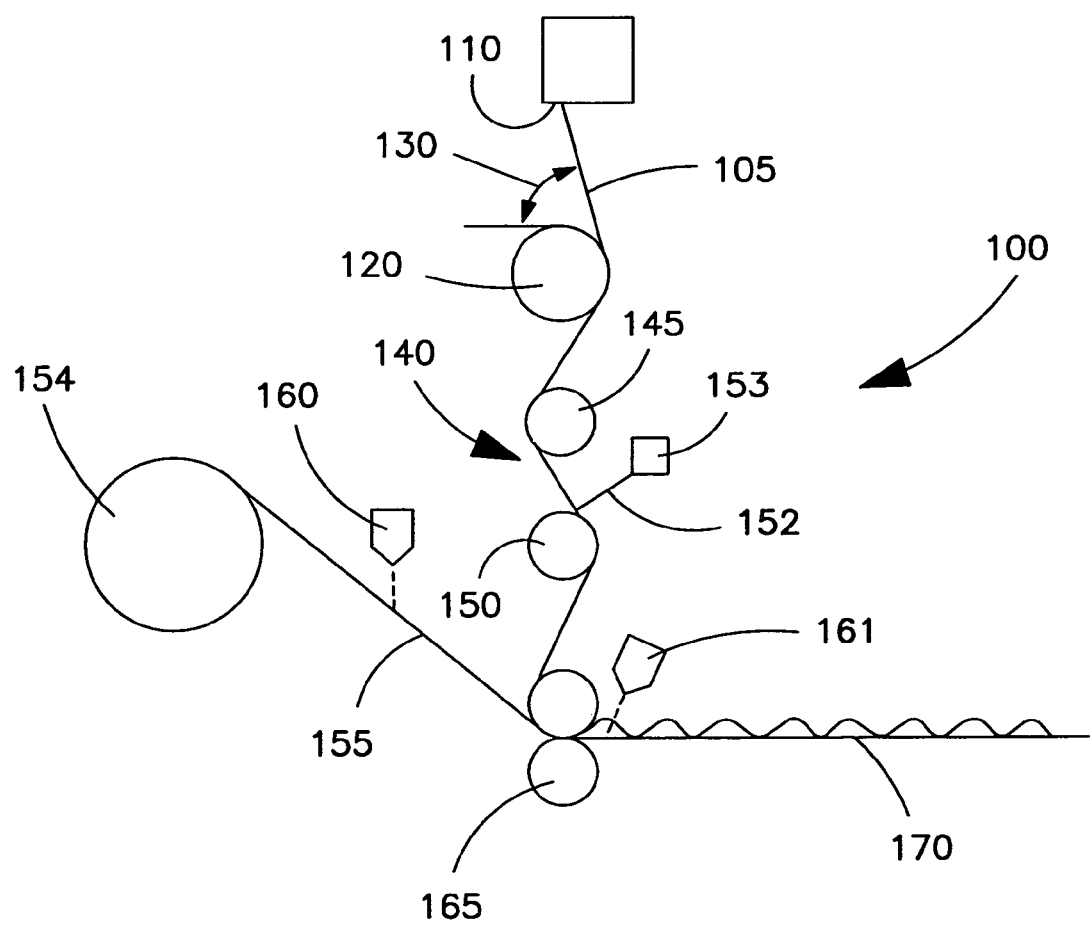
FIG. 6 illustrates an alternative method of manufacturing a single sided stretch bonded laminate in accordance with the invention.

FIG. 6 schematically illustrates a vertical filament laminate manufacturing process 100 for the manufacture of elastic laminates 170 produced from an elastic composition. Referring to FIG. 6, at least one molten elastomeric material 105, i.e. a styrenic block co-polymer material, is extruded from a die extruder 110 through spinning holes as a plurality of substantially continuous elastomeric filaments. The extruder may be extruding at temperatures between about 360 and 500° F. A film die for producing sheets or ribbons may also be used in alternative embodiments. The filaments 105 are quenched and solidified by passing the filaments 105 over a first chill roll 120. Any number of chill rolls can be used. Suitably, chill rolls may have a temperature of between about 40° F. to about 80° F.

The die of the extruder 110 may be positioned with respect to the first roll so that the continuous filaments meet this first roll 120 at a predetermined angle 130. This strand extrusion geometry is particularly advantageous for depositing a melt extrudate onto a rotating roll or drum. An angled, or canted orientation provides an opportunity for the filaments to emerge from the die at a right angle to the roll tangent point, resulting in improved spinning, more efficient energy transfer, and generally longer die life. This configuration allows the filaments to emerge at an angle from the die and follow a relatively straight path to contact the tangent point on the roll surface. The angle 130 between the die exit of the extruder 110 and the vertical axis (or the horizontal axis of the first roll, depending on which angle is measured) may be as little as a few degrees or as much as 90 degrees. For example, a 90 degree extrudate exit to roll angle could be achieved by positioning the extruder 110 directly above the downstream edge of the first roll 120 and having a side exit die tip on the extruder. Moreover, angles such as about 20 degrees, about 35 degrees, or about 45 degrees, away from vertical may be utilized. It has been found that, when utilizing a 12-filament/inch spinplate hole density, an approximately 45 degree angle (shown in FIG. 6) allows the system to operate effectively. The optimum angle, however, may vary as a function of extrudate exit velocity, roll speed, vertical distance from the die to the roll, and horizontal distance from the die centerline to the top dead center of the roller. Optimal performance can be achieved by employing various geometries to result in improved spinning efficiency and reduced filament breakage.

After the filaments 105 are quenched and solidified they are stretched or elongated using a first series of stretch rolls 140. The first series of stretch rolls may comprise one or more individual stretch rolls 145, 150 which rotate at a speed greater than a speed at which chill roll 120 rotates, thereby stretching the filaments 105.

In one embodiment of this invention, each successive roll rotates at a speed greater than the speed of the previous roll. For example, referring to FIG. 6, if the chill roll 120 rotates at a speed "x"; stretch roll 145 rotates at a still greater speed, for example about 1.15x; second stretch roll 150 rotates at a still greater speed, for example about 1.25x to about 7x. As a result, the filaments 105 may be stretched by about 100% to about 800% of an initial pre-stretched length.

After the filaments 105 are stretched, the filaments 105 and the meltblown layer 152 are laminated to a facing material 155 (when filaments are still in a stretched condition, as similarly described in the horizontal platform previously) by an adhesive process as exemplified by the illustrated adhesive distribution unit 160, shown as applying adhesive to the facing material 155. The meltblown layer 152 may be applied to the filaments from extrusion bank 153 between the facing material 155 and the filaments 105, as shown in FIG. 6.

The facing material 155 is unwound from a roll 154 and laminated to a first side of the filaments 105. Before the facing material 155 is laminated to the filaments, it may be necked by additional rolls (not shown). As previously described, the facing material may be a nonwoven material, or laminates thereof, according to the present invention. The laminate material is then passed through nip rolls 165 to bond the elastic filaments 105 and the meltblown layer 152 to the facing 155 by adhesion. The nip rolls 165, may alternatively be used in place of, or in addition to, the stretch rolls 145, 150 to achieve stretching. The laminate material is then allowed to relax thereby allowing the retracting elastomeric filaments to form gathers in the laminate material, as with the previously described horizontal manufacturing platform. It should be noted that in an alternative embodiment, additional relatively low open time adhesive (or nonblocking agent) 161 can be applied following the exit of the bonded elastic layer and facing from a nip 165, such than an additional layer of non-tacky material is deposited on the elastic layer on a side opposite to that of the facing layer, desirably while such laminate is in the stretched condition.

The nip rollers may be designed to provide a patterned roller which may yield certain benefits such as increased bulk or stretching of the laminate and may be used where the strength of the contact adhesion between the facing and the strands is not unduly affected. The calender rolls can be heated to a degree below the melting/softening points of the various laminate components, or may be ambient, or chilled.

Such single sided facing stretch bonded laminate materials have particular effectiveness for use in personal care products to provide elastic attributes to such products. Such single sided facing materials can provide higher extensibility in either the MD or CD direction than a laminate with facings applied to two opposing surfaces of an elastic layer, and can also provide a highly corrugated appearance and a softer feel.

Such material may be useful in providing elastic waist, leg cuff/gasketing, stretchable ear, side panel or stretchable outer cover applications. While not intending to be limiting, FIG. 7 is presented to illustrate the various components of a personal care product, such as a diaper, that may take advantage of such elastic materials. Other examples of personal care products that may incorporate such materials are training pants (such as in side panel materials) and feminine care products. By way of illustration only, training pants suitable for use with the present invention and various materials and methods for constructing the training pants are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al.; and U.S. Pat. No. 6,645,190 issued Nov. 11, 2003 to Olson et al., which are each incorporated herein by reference in its entirety.

With reference to FIG. 7, the disposable diaper 250 generally defines a front waist section 255, a rear waist section 260, and an intermediate section 265 which interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area which is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 7, the diaper 250 may include leg elastics 290 which are constructed to operably tension the side margins of the diaper 250 to provide elasticized leg bands which can closely fit around the legs of the wearer to reduce leakage and provide improved comfort and appearance. Waist elastics 295 are employed to elasticize the end margins of the diaper 250 to provide elasticized waistbands. The waist elastics 295 are configured to provide a resilient, comfortably close fit around the waist of the wearer.

The single sided stretch bonded laminates of the inventive structure and methods are suitable for use as the leg elastics 290 and waist elastics 295. Exemplary of such materials are laminate sheets which either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastomeric by use of a single sided stretch bonded laminate made from the inventive structure. Examples of absorbent articles that include elasticized side panels and selectively configured fastener tabs are described in PCT Patent Application No. WO 95/16425 to Roessler; U.S. Pat. No. 5,399,219 to Roessler et al.; U.S. Pat. No. 5,540,796 to Fries; and U.S. Pat. No. 5,595,618 to Fries each of which is hereby incorporated by reference in its entirety.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 7, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge which is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to K. Enloe.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the instant invention which may include other components suitable for use on diapers are described in U.S. Pat. No. 4,798,603 to Meyer et al.; U.S. Pat. No. 5,176,668 to Bemardin; U.S. Pat. No. 5,176,672 to Bruemmer et al.; U.S. Pat. No. 5,192,606 to Proxmire et al. and U.S. Pat. No. 5,509,915 to Hanson et al. each of which is hereby incorporated by reference in its entirety.

The various components of the diaper 250 are assembled together employing various types of suitable attachment means, such as adhesive bonding, ultrasonic bonding, thermal point bonding or combinations thereof. In the shown embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

It should be appreciated that such single side facing stretch bonded laminate materials may likewise be used in other personal care products, protective outerwear, protective coverings and the like. Further such materials can be used in bandage materials for both human and animal bandaging products. Use of such materials provide acceptable elastic performance at a-lower manufacturing cost.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

Test Method Procedures

Stretch-to-Stop Test

"Stretch-to-stop" refers to a ratio determined from the difference between the unextended dimension of a stretchable laminate and the maximum extended dimension of a stretchable laminate upon the application of a specified tensioning force and dividing that difference by the unextended dimension of the stretchable laminate. If the stretch-to-stop is expressed in percent, this ratio is multiplied by 100. For example, a stretchable laminate having an unextended length of 5 inches (12.7 cm) and a maximum extended length of 10 inches (25.4 cm) upon applying a force of 750 grams has a stretch-to-stop (at 750 grams) of 100 percent. Stretch-to-stop may also be referred to as "maximum non-destructive elongation." Unless specified otherwise, stretch-to-stop values are reported herein at a load of 750 grams. In the elongation or stretch-to-stop test, a 3-inch by 7-inch (7.62 cm by 17.78 cm) sample, with the larger dimension being the machine direction, the cross direction, or any direction in between, is placed in the jaws of a Sintech machine using a gap of 5 cm between the jaws. The sample is then pulled to a stop load of 750 gms with a crosshead speed of about 20 inches/minute (50.8 cm/minute). For the stretchable laminate material of this invention, it is desirable that it demonstrate a stretch to stop value between about 30-400 percent, alternatively between about 50 and 300 percent, still in a further alternative, between about 80-250 percent. The stretch to stop test is done in the direction of extensibility (stretch). Depending upon the material being tested, a greater applied force may be more appropriate. For example, for a single faced laminate the applied force of 750 grams per 3 inch cross-directional width is typically appropriate; however, for certain laminates, particularly higher basis weight laminates, an applied force between 750 and 2000 grams per 3 inch cross-directional width may be most appropriate.

Roll-Blocking Test Method (for Inter-layer Peel Strength of Laminate Layers off of a Roll)

An approximately 50 inch outer diameter roll of single sided stretch bonded laminate was cut along the cross or transverse direction from the top of a roll to the core with a utility knife. Three sections of material from the top, the core and a midpoint of the radius were used as samples. Each sample was approximately 18 inches by 24 inches and contained approximately 30 undisturbed layers of laminate. From each of these samples, eight 3 inch wide by 7 inch long specimens were cut, with the 7 inch being in the machine direction. Each specimen contained 2 layers of laminate (with each laminate including an elastic layer and a single facing layer). The upper layer of one end of the specimen (a full laminate of an elastic layer and facing) was loaded into the upper jaw of a tensile testing unit (Sintech) while the lower layer of the specimen (a full laminate of an elastic layer and facing) from the same end of the specimen as used for the upper layer, was loaded into the lower jaw of the Sintech unit. Using the method described generally below, the Sintech tensile tester (manufactured by MTS Systems Corp., model Synergie 200) was used to measure the average force along the MD length of the material required to separate the two layers, at a 180 degree angle and at a strain rate of 300 mm/min. All specimens were tested in the machine direction. For the samples tested, the polymer used for the filaments in the roll (of continuous filaments) was KRATON G2755, as will be described below. The basis weight ratio of strands to meltblown in the elastic layer was about 90:10. Eight specimens were used and the average value of these was taken as the accepted peel value.

Essentially the test measures the force required to separate two complete layers of single sided stretch bonded laminate material from each other (simulating unwinding of laminate from a supply roll). It is considered that such force would be representative of the force necessary to pull a layer of a rolled material off of the roll. Results are expressed in units of grams of force, with higher numbers representing a tackier fabric, which adheres to itself on a roll. For the materials of the present invention, in one embodiment, the material demonstrates a peel strength of less than 200 g. For an alternative embodiment, the material demonstrates a peel strength of less than 100 g. In still a further alternative embodiment, the material demonstrates a peel strength of less than 50 g.

In conducting the test, the individual plies of the laminate fabric (that is one single sided laminate and another) are manually separated for a distance of approximately 2-3 inches to give at least 4 inches of working direction, or separation length. One ply of the sample specimen from the same end of the specimen is clamped into each jaw of the tensile tester and the specimen is then subjected to a constant rate of extension. The edges of the sample are desirably clean cut and parallel. Desirably Sintech TestWorks software can be utilized to acquire data for the system. The grips include 1 inch by 4 inch jaw faces, where the 4 inch dimension is the width of the jaw. The tests are conducted at standard laboratory atmosphere-ambient conditions. The sample of the test should measure from about 3-4 inches in the CD and at least 6 inches in the MD. An appropriate load cell should be chosen such that the peak load value will fall between 10 and 90 percent of the full scale load, 25 lbs or less. Desirably a 5 lb load cell is used. Desirably, where possible, the measurement should be started at about 16 mm and ended up to about 170 mm of elongation. The gage length should be set at about 2 inches (distance between jaws).

What is claimed is:

1. An elastic single sided stretch bonded laminate comprising:
   an elastic layer comprising an array of continuous filament strands with an elastic meltblown layer deposited on said continuous filament strands, wherein the elastic meltblown layer comprises an elastic polyolefin-based meltblown polymer having a degree of crystallinity between about 3% and about 40%, the polyolefin-based meltblown polymer comprises at least one of the group consisting of ethylene methacrylate, polyisobutylene and butyl acrylate; and
   a facing layer bonded to only one side of said elastic layer;
   wherein the laminate has an inter-layer peel strength of less than about 70 grams per 3 inches cross-directional width at a strain rate of 300 mm/min and eliminates roll blocking.

2. The elastic laminate of claim 1, wherein the elastic polyolefin-based meltblown polymer has a melt flow rate between about 10 and about 600 grams per 10 minutes.

3. The elastic laminate of claim 1, wherein the elastic polyolefin-based meltblown polymer has a melting/softening point between about 40 and about 160 degrees Celsius.

4. The elastic laminate of claim 1, wherein the elastic polyolefin-based meltblown polymer has a density from about 0.8 to about 0.95 grams per cubic centimeter.

5. The elastic laminate of claim 1, wherein the laminate does not include a nonblocking agent applied to the laminate as a post-calender treatment.

6. The elastic laminate of claim 1, further comprising an adhesive that demonstrates a relatively short open time deposited between the array of continuous filament strands and the elastic meltblown layer, wherein the open time of the adhesive is between about 0.2 seconds and 1 minute.

7. The elastic laminate of claim 1, wherein the elastic meltblown layer is deposited at an add-on between about 1 and about 5 grams per square meter during lamination.

8. An elastic single sided stretch bonded laminate comprising:
   an elastic layer comprising an array of continuous filament strands with a meltblown layer deposited on said continuous filament strands, wherein the continuous filament strands comprise an elastic polyolefin-based polymer having a degree of crystallinity between about 3% and about 40%, the continuous filament strands comprise at least one of the group consisting of ethylene methacrylate, polyisobutylene, and butyl acrylate;
   an adhesive that demonstrates a relatively short open time deposited between the array of continuous filament strands and the meltblown layer, wherein the open time of the adhesive is between about 0.2 seconds and 1 minute; and
   a facing layer bonded to only one side of said elastic layer;
   wherein the laminate has an inter-layer peel strength of less than about 70 grams per 3 inches cross-directional width at a strain rate of 300 mm/min and eliminates roll blocking.

9. The elastic laminate of claim 8, wherein the elastic polyolefin-based polymer has a melt flow rate between about 10 and about 600 grams per 10 minutes.

10. The elastic laminate of claim 8, wherein the elastic polyolefin-based polymer has a melting/softening point between about 40 and about 160 degrees Celsius.

11. The elastic laminate of claim 8, wherein the elastic polyolefin-based polymer has a density from about 0.8 to about 0.95 grams per cubic centimeter.

12. The elastic laminate of claim 8, wherein the meltblown layer comprises an elastic polyolefin-based meltblown polymer having a degree of crystallinity between about 3% and about 40%.

13. The elastic laminate of claim 8, wherein the laminate does not include a nonblocking agent applied to the laminate as a post-calender treatment.

14. The elastic laminate of claim 8, wherein the meltblown layer comprises at least two layers, with a first layer comprising an elastic polyolefin-based meltblown polymer having a degree of crystallinity between about 3% and about 40% and a second layer comprising a styrenic block copolymer-based meltblown polymer.

15. The elastic laminate of claim 8, wherein the meltblown layer is deposited at an add-on between about 1 and about 5 grams per square meter during lamination.

16. An elastic single sided stretch bonded laminate comprising:
   an elastic layer comprising an array of continuous filament strands with a meltblown layer deposited on said continuous filament strands, wherein the meltblown layer comprises at least two layers, with a first layer comprising an elastic polyolefin-based meltblown polymer having a degree of crystallinity between about 3% and about 40% and a second layer comprising a styrenic block copolymer-based meltblown polymer, the elastic polyolefin meltblown polymer comprises at least one of the group consisting of ethylene methacrylate, polyisobutylene and butyl acrylate; and
   a facing layer bonded to only one side of said elastic layer, wherein the facing layer comprises an elastic polyolefin-based polymer having a degree of crystallinity between about 3% and about 40%;
   wherein the laminate has an inter-layer peel strength of less than about 70 grams per 3 inches cross-directional width at a strain rate of 300 mm/min and eliminates roll blocking.

17. The elastic laminate of claim 16, wherein the facing layer comprises a spunbond-meltblown-spunbond laminate in which the elastic polyolefin-based polymer of the facing layer is meltblown and positioned between two spunbond layers.

18. The elastic laminate of claim 16, wherein the meltblown layer is deposited at an add-on between about 1 and about 5 grams per square meter during lamination.

19. An elastic single sided stretch bonded laminate comprising:
   an elastic layer comprising an array of continuous filament strands with an elastic meltblown layer deposited on said continuous filament strands, the meltblown layer comprises at least one of the group consisting of ethylene methacrylate, polyisobutylene and butyl acrylate;
   an adhesive that demonstrates a relatively short open time deposited between the array of continuous filament strands and the elastic meltblown layer, wherein the open time of the adhesive is between about 0.2 seconds and 1 minute; and
   a facing layer bonded to only one side of said elastic layer;

wherein the laminate has an inter-layer peel strength of less than about 70 grams per 3 inches cross-directional width at a strain rate of 300 mm/min and eliminates roll blocking.

20. The elastic laminate of claim 19, wherein the elastic meltblown layer comprises an elastic polyolefin-based meltblown polymer having a degree of crystallinity from about 3% to about 40%.

21. The elastic laminate of claim 19, wherein the elastic meltblown layer is deposited at an add-on between about 1 and about 5 grams per square meter during lamination.

22. An elastic single sided stretch bonded laminate comprising:
an elastic layer comprising an array of continuous filament strands with a meltblown layer deposited on said continuous filament strands, wherein the continuous filament strands comprise an elastic polyolefin-based polymer having a degree of crystallinity between about 3% and about 40%, and the meltblown layer comprises at least two layers, with a first layer comprising an elastic polyolefin-based meltblown polymer having a degree of crystallinity between about 3% and about 40% and a second layer comprising a styrenic block copolymer-based meltblown polymers, the first layer comprises at least one of the group consisting of ethylene methacrylate, polyisobutylene and butyl acrylate; and
a facing layer bonded to only one side of said elastic layer;
wherein the laminate has an inter-layer peel strength of less than about 70 grams per 3 inches cross-directional width at a strain rate of 300 mm/min and eliminates roll blocking.

23. The elastic laminate of claim 22, wherein the elastic polyolefin-based polymer in the continuous filament strands has a melt flow rate between about 10 and about 600 grams per 10 minutes.

24. The elastic laminate of claim 22, wherein the elastic polyolefin-based polymer in the continuous filament strands has a melting/softening point between about 40 and about 160 degrees Celsius.

25. The elastic laminate of claim 22, wherein the elastic polyolefin-based polymer in the continuous filament strands has a density from about 0.8 to about 0.95 grams per cubic centimeter.

26. The elastic laminate of claim 1, wherein the elastic meltblown layer comprises at least two layers, with a first layer comprising an elastic polyolefin-based meltblown polymer having a degree of crystallinity between about 3% and about 40% and a second layer comprising a styrenic block copolymer-based meltblown polymer.

27. The elastic laminate of claim 1, further comprising an intra-layer peel strength of about 200 to about 450 grams per 3 inches cross-directional width at a strain rate of 300 mm/min.

28. The elastic laminate of claim 1, further comprising an adhesive that demonstrates a relatively short open time deposited between the array of continuous filament strands and the elastic meltblown layer, wherein the open time of the adhesive is between about 0.2 seconds and 3 seconds.

29. The elastic laminate of claim 28, wherein the adhesive comprises a polypropylene-based hot melt adhesive.

* * * * *